United States Patent
Fisher et al.

(10) Patent No.: US 9,969,714 B2
(45) Date of Patent: May 15, 2018

(54) CARBOXYLIC ACID COMPOUNDS USEFUL FOR INHIBITING MICROSOMAL PROSTAGLANDIN E2 SYNTHASE-1

(71) Applicant: Eli Lilly and Company, Indianapolis, IN (US)

(72) Inventors: Matthew Joseph Fisher, Mooresville, IN (US); Steven Lee Kuklish, Fishers, IN (US); Katherine Marie Partridge, Indianapolis, IN (US); Jeremy Schulenburg York, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days. days.

(21) Appl. No.: 15/520,078

(22) PCT Filed: Oct. 22, 2015

(86) PCT No.: PCT/US2015/056955
§ 371 (c)(1),
(2) Date: Apr. 19, 2017

(87) PCT Pub. No.: WO2016/069374
PCT Pub. Date: May 6, 2016

(65) Prior Publication Data
US 2017/0313679 A1    Nov. 2, 2017

Related U.S. Application Data

(60) Provisional application No. 62/072,140, filed on Oct. 29, 2014.

(51) Int. Cl.
| | |
|---|---|
| *C07D 401/12* | (2006.01) |
| *C07D 401/04* | (2006.01) |
| *C07C 235/40* | (2006.01) |
| *C07D 211/62* | (2006.01) |

(52) U.S. Cl.
CPC .......... *C07D 401/12* (2013.01); *C07C 235/40* (2013.01); *C07D 211/62* (2013.01); *C07D 401/04* (2013.01); *C07C 2601/08* (2017.05); *C07C 2601/14* (2017.05)

(58) Field of Classification Search
CPC .. C07D 401/12; C07D 401/04; C07D 211/62; C07C 235/40; C07C 2601/08; C07C 2601/14
See application file for complete search history.

(56) References Cited

U.S. PATENT DOCUMENTS

| | | |
|---|---|---|
| 2002/0058900 A1 | 5/2002 | Barbut |
| 2006/0128755 A1 | 6/2006 | Nakagawa et al. |
| 2010/0256188 A1 | 10/2010 | Pfau et al. |
| 2010/0324186 A1 | 12/2010 | Birmingham et al. |
| 2011/0263556 A1 | 10/2011 | Priepke et al. |
| 2016/0122330 A1 | 5/2016 | Wannberg |

FOREIGN PATENT DOCUMENTS

| | | |
|---|---|---|
| WO | WO2013146970 | 10/2013 |
| WO | WO2016069376 | 5/2016 |

OTHER PUBLICATIONS

Hamza, BIoorg & MEd Chem, vol. 19, 6077-6086, 2011.*
Kablaoui Natasha et al. "Novel Benzoxazole Inhibitors of mPGES-1" Bioorganic and Medical Chemistry Letters, (2012) vol. 23, p. 907-911.
Bahia et al. "Inhibitors of Microsomal Prostaglandin E2 Synthase-1 Enzyme as Emerging Anti-Inflammatory Candidates", Medicinal Research Reviews (2014), vol. 34(4), p. 825-855.
Shan He et al., Journal of Medicinal Chemistry, (2013) vol. 56, p. 3296-3309.
Iyer, J.P., et al., Expert Opinion on Therapeutic Targets (2009), vol. 13(7), p. 849-865.

* cited by examiner

*Primary Examiner* — D Margaret M Seaman
(74) *Attorney, Agent, or Firm* — Danny L. Wood; James B. Myers

(57) ABSTRACT

The present invention provides compounds of Formula 1, or a pharmaceutically acceptable salts, thereof, where R, X, A, E, and G are as described herein, methods of preparing the compounds, and use of the compounds to treat pain and/or inflammation.

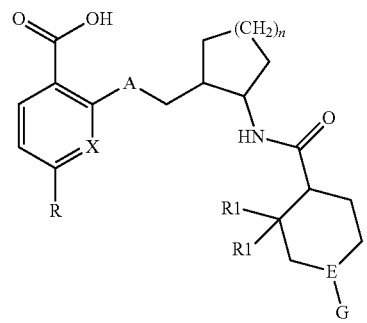

24 Claims, No Drawings

CARBOXYLIC ACID COMPOUNDS USEFUL FOR INHIBITING MICROSOMAL PROSTAGLANDIN E2 SYNTHASE-1

The present invention relates to novel carboxylic acid compounds; to pharmaceutical compositions comprising the compounds; methods of using the compounds to treat pain and/or inflammation associated with arthritis; and intermediates and processes useful in the synthesis of the compounds.

Arthritis involves inflammation of the joints and is often accompanied by pain and stiffness. Osteoarthritis, the most common form of arthritis, is a complex degenerative disease of the joints characterized by progressive destruction of articular cartilage; peri-articular structures including bones, synovium, and associated fibrous joint tissues; and varying degrees of inflammation. Existing drug therapies using non-steroidal, anti-inflammatory drugs (NSAIDs) and cyclooxygenase-2 inhibitors (COX-2 inhibitors) can reduce pain associated with osteoarthritis, but may be only moderately effective over time and each has variable risk/benefit considerations.

The NSAIDs and COX-2 inhibitors reduce inflammation and pain through inhibition of the COX-2 enzymes. In response to pro-inflammatory stimuli, the COX-2 enzymes metabolize arachidonic acid to prostaglandin $H_2$ ($PGH_2$). $PGH_2$ is further metabolized by a variety of enzymes to other eicosanoids including prostaglandin $E_2$ ($PGE_2$), prostaglandin $I_2$ ($PGI_2$), prostaglandin $F_{2\alpha}$ ($PGF_{2\alpha}$), prostaglandin $D_2$ ($PGD_2$), and thromboxane $A_2$ ($TXA_2$). These metabolites are known to induce physiological and pathophysiological effects. It is thought that a drug-mediated imbalance of $PGI_2$ and $TXA_2$ may explain why NSAIDs and COX-2 inhibitors produce deleterious gastrointestinal and cardiovascular side-effects. Consequently, these classes of drugs may be contraindicated for many patients due to pre-existing or emergent cardiovascular and/or gastrointestinal conditions. Additionally, patients can become refractory over time to specific drug treatments.

Of the arachidonic acid metabolites, $PGE_2$ has been identified as an important mediator of conditions associated with osteoarthritis; for example, fever, pain, and inflammation. Prostaglandin $E_2$ is specifically produced through the metabolism of $PGH_2$ by microsomal prostaglandin $E_2$ synthase-1 (mPGES-1). It is thought that selectively inhibiting mPGES-1 may provide a new treatment option for patients suffering from arthritis.

Publication WO 2013/146970 discloses tri-substituted quinoline compounds and suggests that the disclosed compounds may be useful for treating inflammatory diseases inter alia. However, that publication does not disclose compounds as claimed in this application.

There remains a need for additional options to treat the inflammation and alleviate the pain associate with arthritis. The present invention provides novel compounds that inhibit mPGES-1 and that may be beneficial for treating patients suffering from arthritis and, in particular, osteoarthritis.

The present invention provides compounds of Formula 1, or a pharmaceutically acceptable salt thereof,

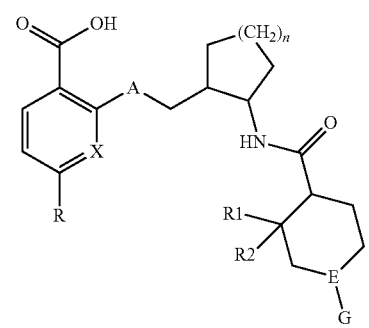

where: n is 1 or 2; A is selected from: —$CH_2$—, —NH—, and —O—; E is —CH— or N; X is N or CH; R is selected from: H, —$CH_3$, F, and Cl; and R1 and R2 are independently H or —$CH_3$; G is selected from:

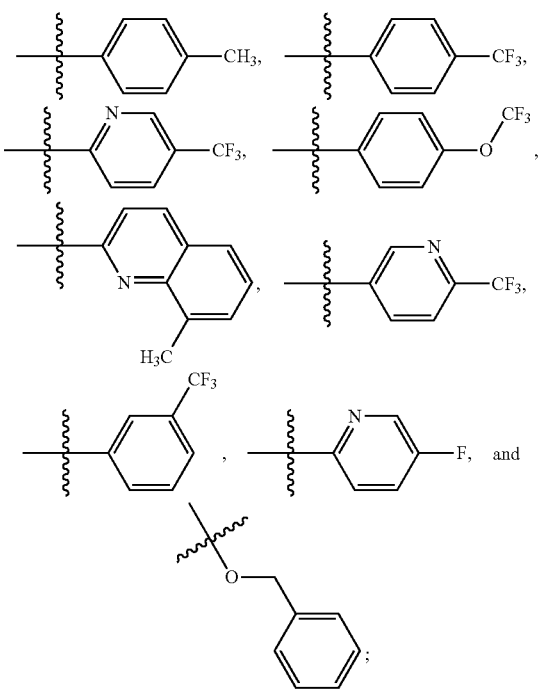

provided that when G is

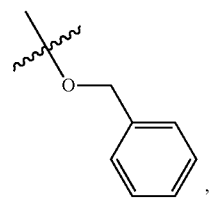 [SMILES: *OCc1ccccc1]

E is CH; and provided that when A is —NH— or —O—, X is CH.

The present invention also provides a compound according to Formula 2, or a pharmaceutically acceptable salt thereof,

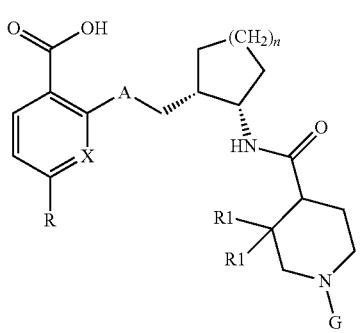

where: n is 1 or 2; A is selected from: —CH₂—, —NH—, and —O—; X is N or CH; R is selected from: H, —CH₃, F, and Cl; and each R1 is independently selected from H or —CH₃; G is selected from:

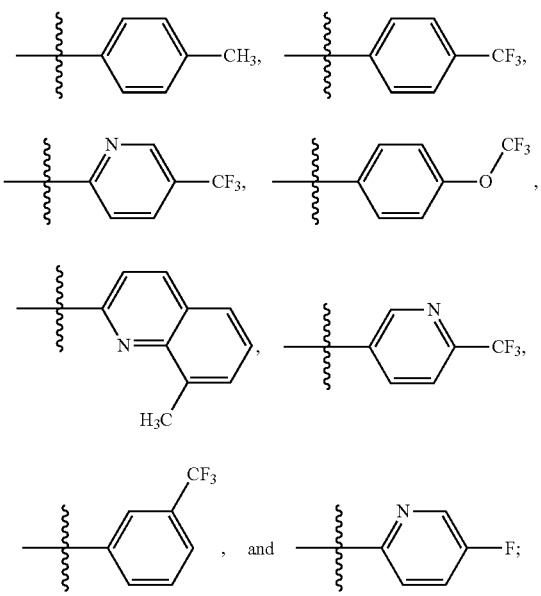

provided that when A is —NH— or —O—, X is —CH—.

In another form, the present invention provides a compound according to Formulae 1 or 2, or a pharmaceutically acceptable salt thereof, where n is 1.

In another form, the present invention provides a compound according to Formulae 1, or a pharmaceutically acceptable salt thereof, where E is N.

In another form, the present invention provides a compound according to Formulae 1 or 2, or a pharmaceutically acceptable salt thereof, where R is selected from: H, —CH₃, and F. For more preferred compounds of the invention, R is H.

In another form, the present invention provides a compound according to Formulae 1 or 2, or a pharmaceutically acceptable salt thereof, where A is —O— or —CH₂—. For more preferred compounds of the invention A is —CH₂—.

In another form, the present invention, provides compounds according to Formula 1 and 2, or a pharmaceutically acceptable salt thereof, where G is selected from:

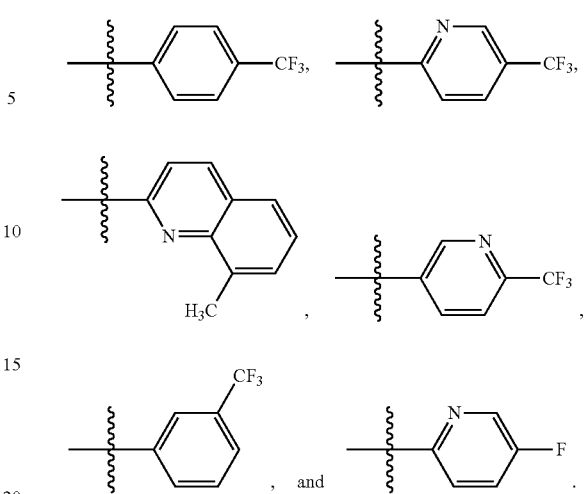

For more preferred compounds of the invention, G is selected from:

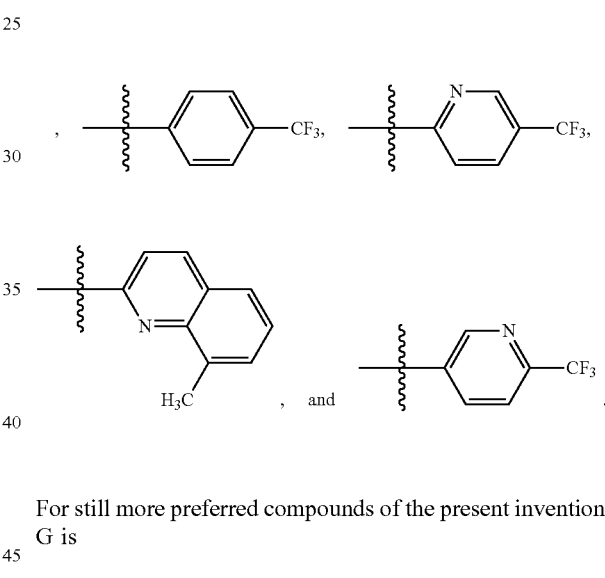

For still more preferred compounds of the present invention, G is

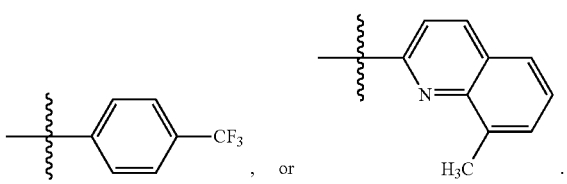 [SMILES: *c1ccc(C(F)(F)F)cc1 ; *c1ccc2cccc(C)c2n1]

In another form, the present invention provides a compound according to Formulae 1 or 2, or a pharmaceutically acceptable salt thereof where X is —CH—.

In another form, the present invention provides a compound according to Formulae 1 or 2, or a pharmaceutically acceptable salt thereof where R1 and R2 are H.

In another form, the present invention provides a compound according to Formula 3, or a pharmaceutically acceptable salt thereof.

3

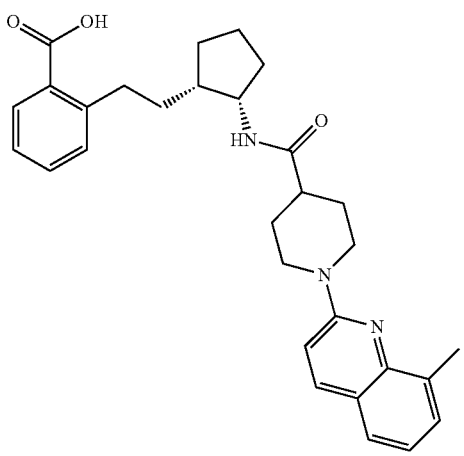

In another form, the present invention provides a pharmaceutically acceptable salt of a compound of Formulae 1, 2 or 3 wherein the pharmaceutically acceptable salt is prepared by the addition of a base such as sodium hydroxide or potassium hydroxide. In one embodiment, a compound according to Formulae 1, 2 or 3 is provided as a sodium salt.

In another form, the present invention provides a pharmaceutically acceptable composition comprising a compound according Formulae 1, 2, or 3, or a pharmaceutically acceptable salt thereof, and at least one of a pharmaceutically acceptable carrier, diluent, or excipient.

The present invention also provides a method of treating a patient in need of treatment for pain associated with arthritis. The method comprises administering to the patient an effective amount of a compound according to Formulae 1, 2, or 3, or a pharmaceutically acceptable salt thereof. The present invention further provides a method for treating the pain associated with osteoarthritis. The method comprises administering to a patient an effective amount of a compound thereof according to Formulae 1, 2, or 3, or a pharmaceutically acceptable salt thereof.

The present invention also provides a method of treating a patient in need of treatment for inflammation associated with arthritis, the method comprising administering to the patient an effective amount of a compound according to Formulae 1, 2, or 3, or a pharmaceutically acceptable salt thereof. The present invention also provides a method of treating inflammation associated with osteoarthritis. The method comprises administering to the patient in need of treatment an effective amount of a compound according to Formulae 1, 2, or 3, or a pharmaceutically acceptable salt thereof.

The present invention also provides a method for treating a patient in need of treatment for pain or inflammation associated with arthritis. The method comprises administering to the patient a pharmaceutically acceptable composition containing an effective amount of a compound according to Formulae 1, 2, or 3, or a pharmaceutically acceptable salt thereof.

The present invention also provides a method of treating a patient in need of treatment for pain or inflammation associated with osteoarthritis. The method comprises administering to the patient a pharmaceutically acceptable composition containing an effective amount of a compound according to Formulae 1, 2, or 3, or a pharmaceutically acceptable salt thereof.

The present invention also provides a compound according to Formulae 1, 2, or 3, or a pharmaceutically acceptable salt thereof, for the preparation of a medicament.

The present invention also provides a compound according to Formulae 1, 2, or 3, or a pharmaceutically acceptable salt thereof, for use in therapy.

The present invention also provides a compound according to Formulae 1, 2 or 3, or a pharmaceutically acceptable salt thereof, for use in the treatment of pain associated with arthritis. In another form, the present invention also provides a compound according to Formulae 1, 2, or 3 or a pharmaceutically acceptable salt thereof, for use in the treatment of pain associated with osteoarthritis.

The present invention also provides a compound, or a pharmaceutically acceptable salt thereof, according to Formulae 1, 2, or 3 for use in the treatment of inflammation associated with arthritis. In another form, the present invention provides a compound according to Formula 1, 2, or 3 or a pharmaceutically acceptable salt thereof, for use in the treatment of inflammation associated with osteoarthritis.

The present invention also provides the use of a compound according to Formulae 1, 2, or 3 or a pharmaceutically acceptable salt thereof, for the manufacture of a medicament. In one embodiment, the medicament is to treat pain associated with arthritis. In another embodiment, the medicament is to treat pain associated with osteoarthritis.

The present invention also provides the use of a compound according to Formulae 1, 2, or 3, or a pharmaceutically acceptable salt thereof, for the manufacture of a medicament. In one embodiment, the medicament is to treat inflammation associated with arthritis. In another embodiment the medicament is to treat inflammation associated with osteoarthritis.

The present invention also provides a compound according to Formula 4

4

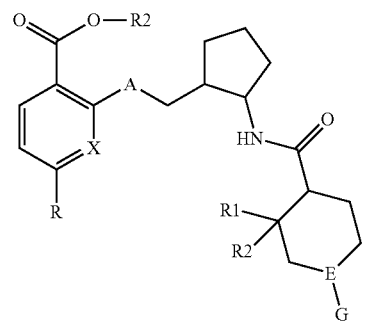

where R, X, A, E, and G are as described above and R2 is selected from: $C_{1-4}$ alkyl, —$CH_2CH$=$CH_2$, $C_{1-4}$ haloalkyl, $C_{3-6}$cycloalkyl, $C_{1-4}$alkyl-$C_{3-6}$cycloalkyl, phenyl, or $C_{1-5}$ alkylphenyl, and tetrahydropyrane.

As used herein, the terms "treating" or "to treat" includes stopping or reducing the severity of an existing symptom or disorder, in particular the pain and/inflammation, associated with arthritis or preferable osteoarthritis.

As used herein, the term "patient" refers to a mammal, such as a human, as well as a mouse, guinea pig, rat, dog, cat, cow, horse, sheep, and goat or fowl, such as chicken and duck. The preferred patient is a human.

The exemplified compounds of the present invention can be formulated into pharmaceutical compositions in accordance within accepted practices. Examples of pharmaceutically acceptable carriers, excipients, and diluents can be found in Remington's Pharmaceutical Sciences, Gennaro, Ed., Mack Publishing Co. Easton Pa., 1990. Non-limiting examples include the following: starch, sugars, mannitol, and silica derivatives; binding agents such as carboxymethyl cellulose and other cellulose derivatives, glycerol monostearate; adsorptive carriers such as kaolin and bentonite; and lubricants such as talc, calcium, and magnesium stearate, and solid polyethyl glycols. In one form, the pharmaceutical formulation includes 20% Captisol™ in 500 mM pH 8 phosphate buffer.

Preferred pharmaceutical compositions can be formulated as a tablet or capsule for oral administration or as an injectable solution. The tablet, capsule, or solution will include a compound of the present invention in an amount effective for treating a patient in need of treatment.

As used herein, the term "effective amount" refers to the amount or dose of a compound of the invention, or a pharmaceutically acceptable salt thereof, which upon a single or multiple dose administration to the patient, provides the desired effect, such as the reduction or elimination of pain and/or inflammation in the patient under diagnosis or treatment.

An effective amount can be readily determined by the attending physician, veterinarian, or other diagnostician by using known techniques and by observing results obtained under analogous circumstances. In determining the effective amount for a patient, a number of factors can be considered, including, but not limited to: the species of mammal, fowl, or livestock; its size, age, and general health; the specific disease or disorder involved, e.g., pain and/or inflammation associated with arthritis or osteoarthritis; the degree of or involvement or the severity of the disease or disorder; the response of the individual patient; the mode of administration; the bioavailability characteristics of the compound of Formula 1, or its pharmaceutically acceptable salt, as a formulated drug product in the dose regimen selected; the use of concomitant medication; and other relevant circumstances.

In one embodiment, the effective amount can be from about 0.0005 mg per kg of body weight to about 100 mg/kg. More preferably, the effective amount can be from about 0.001 mg/kg to about 50 mg/kg. Still more preferably, the effective amount can be from about 0.001 mg/kg to about 20 mg/kg.

A compound of the present invention can be combined with other treatment methods and/or additional therapeutic agents, preferably agents for the treatment of arthritis and/or osteoarthritis. Examples include NSAIDs or COX-2 inhibitors, such as ibuprofen, aspirin, acetaminophen, celecoxib, naproxen, and ketoprofen; opiods, such as oxycodone and fentanyl; and corticosteroids, such as hydrocortisone, prednisolone, and prednisone.

The exemplified compounds and the additional therapeutic agent(s) can be administered either together through the same delivery route and device such as a single pill, capsule, tablet or solution; or separately administered either at the same time in separate delivery devices or sequentially.

The compounds of the present invention can be provided as a pharmaceutically acceptable salt. "Pharmaceutically acceptable salt" refers to salts of the compound of the invention considered to be acceptable for clinical and/or veterinary use. Pharmaceutically acceptable salts and common methodology for preparing them are well known in the art.

See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The compounds of the present invention, or a salt thereof, may be prepared by a variety of procedures known in the art, some of which are illustrated in the Schemes, Preparations, and the Examples below. One of ordinary skill in the art will recognize that the specific synthetic steps for each of the routes described may be combined in different ways, or in conjunction with steps from different schemes, to prepare compounds of the invention, or salts thereof. The products of each step in the schemes below can be recovered or purified by conventional methods, including extraction, evaporation, precipitation, chromatography, supercritical fluid chromatography, filtration, trituration, and crystallization.

Individual isomers, enantiomers, or diastereomers may be separated or resolved by one of ordinary skill in the art at any convenient point in the synthesis by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). Additionally, the intermediates described in the following preparations contain nitrogen and oxygen protecting groups. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

The reagents and starting materials are generally readily available to one of ordinary skill in the art. Others may be made by standard techniques of organic and heterocyclic chemistry or by the procedures described in the Preparations and the Examples.

The depiction of a bond with a jagged line through it as illustrated below indicates the point of attachment of the substituent to the rest of the molecule.

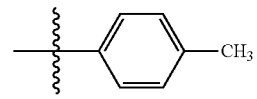 [SMILES: *c1ccc(C)cc1]

The depiction of a crossed bond  indicates a mixture of E, Z diastereomers.

The abbreviations used herein are defined according to *Aldrichimica Acta*, Vol. 17, No. 1, 1984. Other abbreviations are defined as follows: "δ" refers to parts per million down-field from tetramethylsilane; "ATCC" refers to American type culture collection; "BOP" refers to (benzotriazol-1-yloxy)tris(dimethylamino)phosphonium hexafluorophosphate; "BSA" refers to Bovine Serum Albumin; "CDI" refers 1,1'-carbonyldiimidazole; "DCC" refers to 1,3-dicyclohexylcarbodiimide; "DIC" refers to 1,3-diisopropylcarbodiimide; "DMSO" refers to dimethylsulfoxide; "EDCI" refers to 1-(3-dimethylaminopropyl)-3-ethylcarbodiimide hydrochloride; "EDTA" refers to ethylenediaminetetraacetic acid; "EIA" refers to enzyme immune-assay; "EMS" refers to electron ionized mass spectrometry; "ESMS" refers to electrospray mass spectrometry; "EtOAc" refers to ethyl acetate; "HATU" refers to (dimethylamino)-N,N-dimethyl (3H-[1,2,3]triazolo[4,5-b]pyridin-3-yloxy)methaniminium hexafluorophosphate; "HBTU" refers to (1H-benzotriazol-1-yloxy)(dimethylamino)-N,N-dimethylmethaniminium hexafluorophosphate; "HOAT" refers to 1-hydroxy-7-azobenzotriazole; "HOBT" refers to 1-hydroxylbenzotriazole hydrate; "IC$_{50}$" refers to the concentration of an agent that produces 50% of the maximal inhibitory response possible for that agent; "LPS" refers to lipopolysaccharide; "NSAID" refers to a nonsteroidal anti-inflammatory drug; "PBS" refers to phosphate buffered saline; "PGE$_2$" refers to prostaglandin E$_2$; "PGH$_2$" refers to prostaglandin H$_2$; "PGI$_2$" refers to prostaglandin I$_2$; "PyBOP" refers to (benzotriazol-1-yl-oxytripyrrolidinophosphonium hexafluorophosphate); "PyBrOP" refers to bromo(tri-pyrrolidinyl)phosphonium hexafluorophosphate; "rhIL-1β" refers to recombinant human interleukin 1β; "SFC" refers to supercritical fluid chromatography; "TBME" refers to t-butyl methyl ether; and "t$_R$" refers to retention time.

The following schemes, preparations and Examples further illustrate the invention.

acid source such as acetic acid and a reducing agent such as sodium triacetoxyborohydride at about 0° C. to room temperature with or without heating to about 60° C. to give the coupled product of Step 4, substep 1. This product can then be deprotected under conditions well known in the art such as using iodotrimethylsilane to remove the amine protecting group or under acidic conditions such as using a 4 M HCl solution in 1,4-dioxane to give the product of Step 4, substep 2. In Step 3, substep 1, when A=CH$_2$, the double bond of the Step 2 product can be reduced under conditions well known in the art such as hydrogenation with a catalyst of 5%-10% Pd/C or 5% Pt/C in a solvent such as EtOAc and/or methanol at about 101 to 413 kPa to give the product of Step 3. A person skilled in the art will realize there are different Pd catalysts, solvent conditions, and hydrogenation conditions that can be used to reduce double bonds. The product of Step

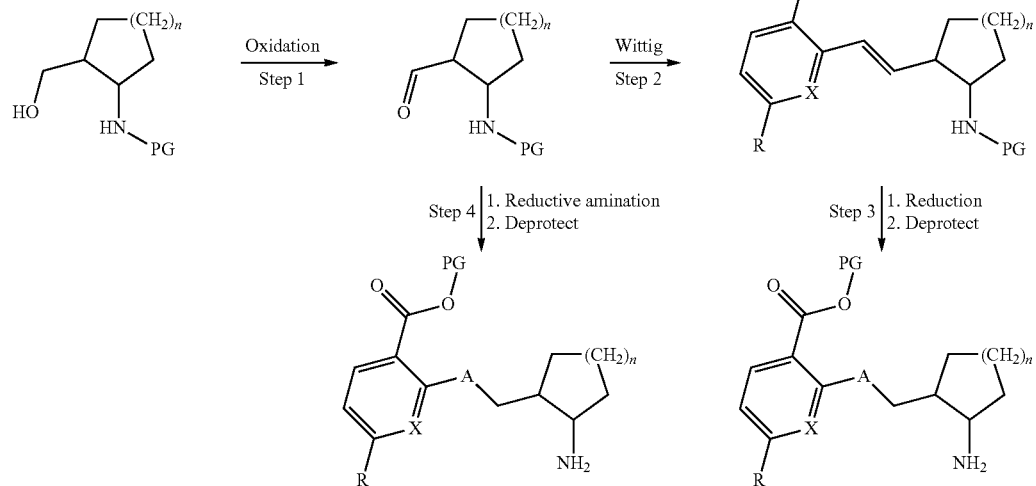

Scheme 1

PG = protecting group

In Scheme 1, Step 1, an oxidation of a primary alcohol is accomplished under conditions well known in the art, for example, using Dess-Martin Periodinane™ as an oxidizing agent to provide the aldehyde product of Step 1. "PG" is a protecting group developed for amino or carboxy groups, such as carbamates, amides, and esters Such protecting groups are well known and appreciated in the art. Alternatively 2,2,6,6-tetramethylpiperidine-N-oxide can be used as an oxidizing agent with potassium bromide and the mixture can be cooled to about −10° C. followed by the addition of sodium hypochlorite to give the aldehyde product of Step 1. When A=CH$_2$, the aldehyde can be reacted with an appropriate Wittig reagent along with a base such as potassium tert-butoxide to give the alkene product of Step 2. The Wittig product of Step 2 can be prepared by treating the appropriate (5-substituted-2-protected carboxy)benzyl or pyridyl triphenylphosphonium bromide with a strong base at a temperature of about 0° C., followed by the dropwise addition of a 2-formylcycloalkyl carbamate. Alternatively, in Step 4, when A=N, the aldehyde can be treated under reductive amination conditions with the appropriate aniline with an 3, substep 1 can be deprotected in substep 2 as described in Scheme 1, substep 2 to give the product of Step 3, substep 2.

Scheme 2

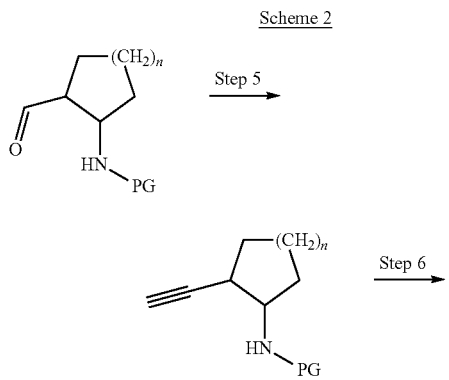

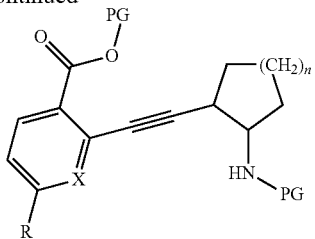

Step 7 | 1. Reduction
       | 2. Deprotection

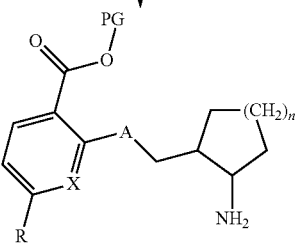

Alternatively, in Scheme 2, the aldehyde of Step 1, Scheme 1 can be converted to a triple bond with 1-diazo-1-dimethoxyphosphoryl-propan-2-one and an inorganic base such as potassium carbonate in a solvent such as methanol to give the product of Step 5. The product of Step 5 can then be coupled under palladium conditions with an optionally substituted halobenzoate (such as an iodobenzoate) in a solvent such as tetrahydrofuran along with copper (I) iodide and a palladium catalyst such as bis(triphenylphosphine)palladium(II) chloride to give the product of Step 6. The triple bond can be reduced as described in Scheme 1, Step 3, substep 1 under hydrogenation conditions to give the product of Step 7, substep 1. The amine can then be deprotected as described in Scheme 1, Step 4, substep 2 to give the product of Step 7, substep 2.

Scheme 3

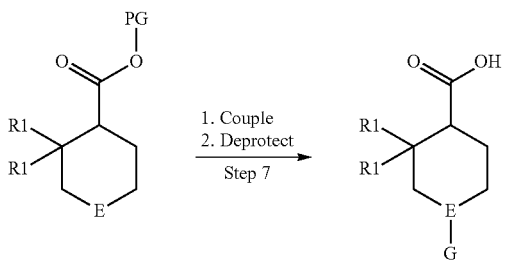

For E = N

In Scheme 3, where E=NH, a 3-substituted carboxy protected piperidine undergoes a nucleophilic aromatic substitution with a halogen-substituted G group under a variety of conditions. For example, an inorganic base such as potassium carbonate or an organic base such as N,N-diisopropylethylamine or pyridine and heating to about 130-150° C. to give the product of Step 8, substep 1. This can be followed by deprotection of the piperidine carboxy group under standard conditions with an inorganic base such as aqueous sodium hydroxide or lithium hydroxide in a solvent such as methanol and tetrahydrofuran to give the product of Step 8, substep 2. Acidic conditions such as 1 N HCl, 4 M HCl in 1,4-dioxane, or aqueous sulfuric acid can also be used to deprotect the protected carboxy group. The nucleophilic aromatic substitution can also be accomplished under neat conditions using a microwave and heating to about 200° C. to give the product of Step 8, substep 1. Alternatively, a substituted 4-carboxy piperidine can be coupled using palladium and a base, such as, sodium tert-butoxide and a catalyst such as (2-dicyclohexylphosphino-2',6'-diisopropoxy-1,1'-biphenyl)[2-(2'-amino-1,1'-biphenyl)]palladium(II) methanesulfonate, under refluxing conditions to give the product of Step 8 where the carboxylic acid is not protected.

Scheme 4

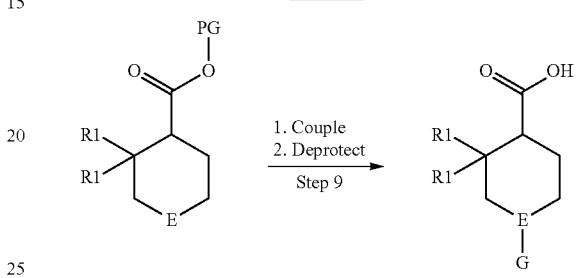

For E = CHOH intermediate

In Scheme 4, where E=CHOH, an intermediate 4-carboxy protected cyclohexanol is alkylated with benzyl bromide using an organic base such as diisopropylethylamine to give the product of Step 9 where E=CH(OCH$_2$).

Scheme 5

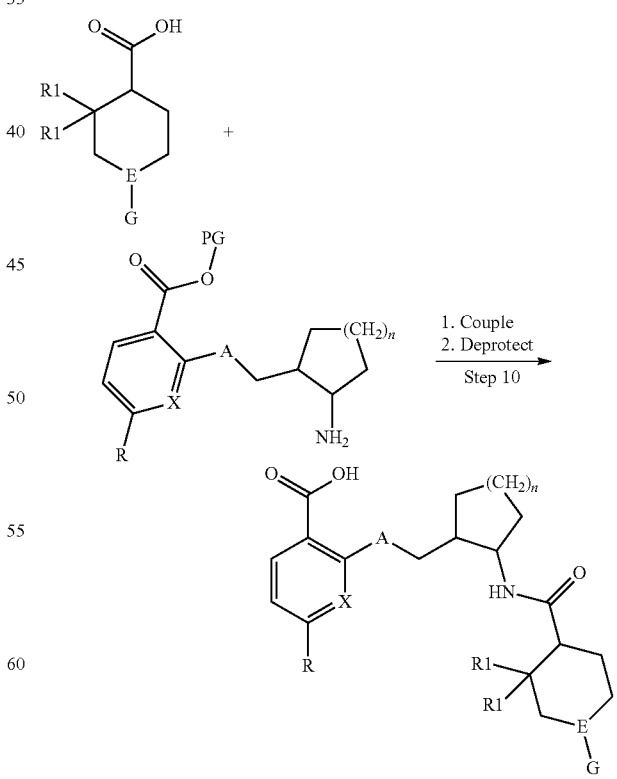

The products of Step 8 and Step 9 can then be reacted with the appropriate product of Scheme 1, Step 4, substep 2; Scheme 1, Step 3, substep 2; or Scheme 2, Step 7, substep 2 under amidation conditions using a base such as diisopropylethylamine, a coupling reagent such as 1-propanephosphonic acid cyclic anhydride to give the product of Step 10, substep 1. One skilled in the art will recognize that there are a number of methods and reagents for amide formation resulting from the reaction of carboxylic acids and amines. For example, the reaction of the amine compound with an appropriate carboxylic acid in the presence of a coupling reagent with or without an organic base such as diisopropylethylamine or triethylamine can provide a compound of Formula 1. Coupling reagents include carbodiimides, such as DCC, DIC, EDCI or a carbonyldiimidazole such as CDI. Amide coupling additives, such as 1-hydroxybenzotriazole hydrate and HOAt can also be used to enhance the reaction. Additionally, uronium or phosphonium salts of non-nucleophilic anions, such as HBTU, HATU, BOP, PyBOP, and PyBrOP could be used in place of the more traditional coupling reagents. An additive such as DMAP may be used to enhance the reaction. The product of Step 10, substep 1 can then be deprotected under basic conditions as described in Scheme 3, Step 8, substep 2 to give the compounds of Formula 1.

A pharmaceutically acceptable salt of the compounds of the invention, such as a hydrochloride salt, can be formed, for example, by reaction of an appropriate free base of Formulae 1, 2, or 3 an appropriate pharmaceutically acceptable acid such as hydrochloric acid in a suitable solvent such as diethyl ether under standard conditions well known in the art. Additionally, the formation of such salts can occur concomitantly with deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The following preparations and examples further illustrate the invention.

PREPARATION 1

(5-Chloro-2-(methoxycarbonyl)benzyl)triphenylphosphonium bromide

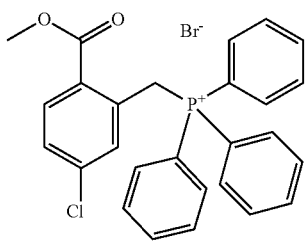 [SMILES: COC(=O)c1ccc(Cl)cc1C[P+](c1ccccc1)(c1ccccc1)c1ccccc1 ; [Br-]]

Combine methyl 2-(bromomethyl)-5-chlorobenzoate (120 g, 455 mmol) and triphenylphosphine (131 g, 501 mmol) in toluene (1.1 L). Heat the mixture to reflux overnight while stirring. Cool the heterogeneous mixture to room temperature. Filter the mixture to collect the white precipitate. Sequentially wash the filter cake with toluene (500 mL) and hexanes (2×500 mL). Dry the solid under vacuum to provide the title compound as a white solid (225 g, 94%). ESMS (m/z) 445 (M⁺)

PREPARATION 2

(5-Fluoro-2-(methoxycarbonyl)benzyl)triphenylphosphonium bromide AVH-E12672-005

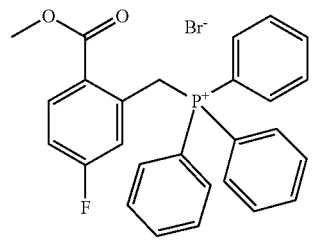 [SMILES: COC(=O)c1ccc(F)cc1C[P+](c1ccccc1)(c1ccccc1)c1ccccc1 ; [Br-]]

Prepare the title compound essentially by the method of PREPARATION 1. ¹H NMR (400 MHz, CDCl₃) δ 7.84 (dd, J=8.8, 5.8 Hz, 1 H), 7.80-7.56 (m, 16H), 7.07-6.99 (m, 1H), 6.20 (d, J=15.4 Hz, 2 H), 3.48 (s, 3H).

PREPARATION 3 tert-Butyl ((1S,2R)-2-formylcyclopentyl)carbamate

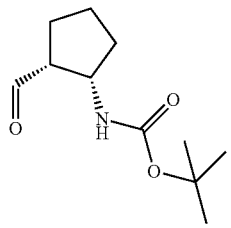

Dissolve tert-butyl ((1S,2R)-2-(hydroxymethyl)cyclopentyl)carbamate (Hanselmann, R. Zhou, J. Ma, P. Confalone, P. N. *J. Org. Chem.* 2003, 68 (22) 8739-8741) (65 g, 0.30 mol) in dichloromethane (1.3 L). Cool the solution to −5° C. and add 3,3,3-triacetoxy-3-iodophthalide (185 g, 436 mmol) in portions. After the addition, dilute the reaction mixture with dichloromethane (2 L). Sequentially wash the mixture with 20 wt % aqueous Na₂S₂O₃ (3×2 L) and saturated aqueous NaHCO₃ (2×2 L). Dry the dichloromethane mixture over Na₂SO₄, filter, collect the filtrate, and remove the solvent under reduced pressure to provide the title compound as an off-white solid, (65 g, 100%). EIMS (m/z) 213 (M⁺).

PREPARATION 4

Methyl 2-(2-((1S,2S)-2-((tert-butoxycarbonyl)amino)cyclopentyl)vinyl)-4-chlorobenzoate)

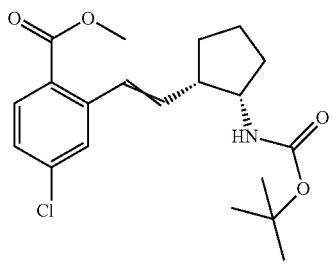 [SMILES: COC(=O)c1ccc(Cl)cc1C=C[C@@H]1CCC[C@@H]1NC(=O)OC(C)(C)C]

Suspend (5-chloro-2-methoxycarbonyl)benzyl)triphenylphosphonium bromide (225 g, 428 mmol) in tetrahydrofuran (1.6 L). Cool the suspension to 0° C. and add potassium tert-butoxide (45 g, 401 mmol) in portions over 2 minutes. Maintain the temperature of the resulting yellow solution at 0° C. Add tert-butyl ((1S,2R)-2-formylcyclopentyl)carbamate (65 g, 305 mmol) as a solution in tetrahydrofuran (300 mL) drop-wise over 20 minutes while maintaining the temperature of the reaction below 5° C. Allow the reaction mixture warm to room temperature and stir overnight. Dilute the reaction mixture with saturated aqueous $NaHCO_3$ (2 L) and extract with EtOAc (2×1.5 L). Combine the organic extracts and wash the combined extracts with water (3 L). Dry the organic layer over $Na_2SO_4$; filter; collect the filtrate; and concentrate under reduced pressure to provide a crude residue. Divide the residue into two portions. Purify the first portion of the crude residue using silica gel chromatography, eluting with a gradient of 25% to 50% hexanes: 10% TMBE in dichloromethane and the second portion with a gradient of 25% to 35% hexanes: 10% TMBE in dichloromethane to provide a 4:1 E:Z mixture of the title compound as a yellow oil that solidifies to a white solid upon standing, (99.5 g, 262 mmol, 86%). ESMS (m/z) 402 $(M+Na)^+$.

The following compounds in Table 1 can be prepared essentially by the method of Preparation 4 using the appropriately substituted triphenylphosphonium bromide reagent.

TABLE 1

| Prep. No. | Chemical name | Structure | ESMS (m/z) |
|---|---|---|---|
| 5[1] | Ethyl 2-(2-((1S,2S)-2-((tert-butoxycarbonyl)amino)cyclopentyl)vinyl)nicotinate (E:Z 1:1) | 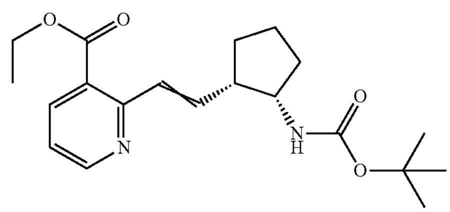 [SMILES: CCOC(=O)c1cccnc1C=C[C@@H]1CCC[C@@H]1NC(=O)OC(C)(C)C] | 361 $(M + H)^+$ |
| 6[2] | Methyl 4-bromo-2-(2-((1S,2S)-2-((tert-butoxycarbonyl)amino)cyclopentyl)vinyl)benzoate | 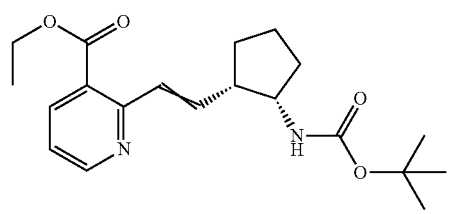 [SMILES: CCOC(=O)c1cccnc1C=C[C@@H]1CCC[C@@H]1NC(=O)OC(C)(C)C] | ($^{79}Br/^{81}Br$) 446/448 $(M + Na)^+$ |
| 7[2] | Methyl 2-(2-((1S,2S)-2-((tert-butoxycarbonyl)amino)cyclopentyl)vinyl)benzoate (E:Z 6:1) | 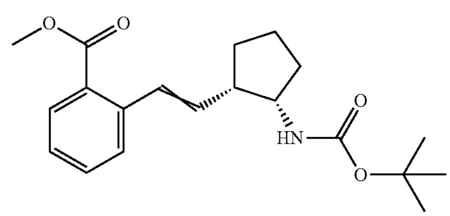 [SMILES: COC(=O)c1ccccc1C=C[C@@H]1CCC[C@@H]1NC(=O)OC(C)(C)C] | 368 $(M + Na)^+$ |
| 8[3] | Methyl 2-(2-((1S,2S)-2-((tert-butoxycarbonyl)amino)cyclopentyl)vinyl)-4-fluorobenzoate | 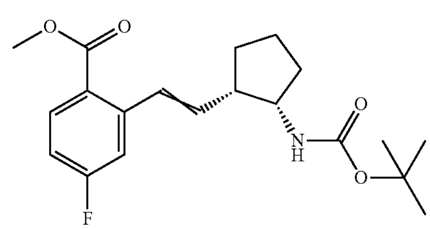 [SMILES: COC(=O)c1ccc(F)cc1C=C[C@@H]1CCC[C@@H]1NC(=O)OC(C)(C)C] | 386 $(M + Na)^+$ |

[1] Chromatography with a gradient of 10% to 50% EtOAc in dichloromethane
[2] Chromatography with a gradient of 10% to 50% EtOAc in hexanes
[3] Chromatography with a gradient of 15% to 60% EtOAc in hexanes

PREPARATION 9

Methyl 2-(2-((1S,2S)-2-((tert-butoxycarbonyl)amino)cyclopentyl)vinyl)-4-methylbenzoate

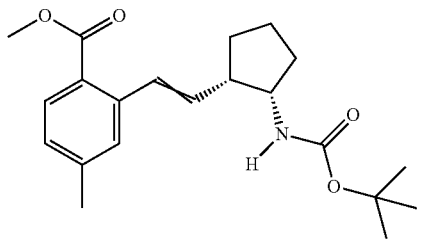 [SMILES: COC(=O)c1ccc(C)cc1C=C[C@@H]1CCC[C@@H]1NC(=O)OC(C)(C)C]

Add methyl 4-bromo-2-(2-((1S,2S)-2-((tert-butoxycarbonyl)amino)cyclopentyl)vinyl) benzoate (0.73 g, 1.72 mmol) and 1,4-dioxane (20 mL) to a microwave vessel; then sparge the vessel with nitrogen for thirty minutes. Add potassium carbonate (310 mg, 2.24 mmol), methylboronic acid (514 mg, 8.59 mmol), and tetrakis(triphenylphosphine)palladium (115 mg, 0.099 mmol). Heat the vessel in a microwave for 45 minutes at 150° C. Combine the resulting crude mixture with two additional lots, prepared essentially by the same procedure, for a combined theoretical yield of 5.13 mmol Partition the combined mixtures between EtOAc and water and separate the organic phase from the aqueous phase. Sequentially wash the organic phase with saturated sodium bicarbonate (2×) and saturated aqueous sodium chloride. Dry the organic phase over MgSO$_4$, filter; collect the filtrate; and concentrate to dryness. Subject the resulting black oil to silica gel column chromatography, eluting with a gradient of 10/90 to 40/60 EtOAc/hexanes, to provide the title compound as a white solid (1.13 g, 3.14 mmol, 61% overall yield). ESMS (m/z) 382 (M+Na)$^+$.

PREPARATION 10

Methyl 2-((((1S,2S)-2-((tert-butoxycarbonyl)amino)cyclopentyl)methyl)amino)-4-chlorobenzoate

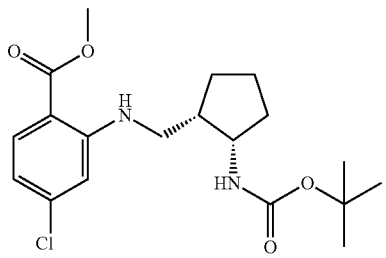 [SMILES: COC(=O)c1ccc(Cl)cc1NC[C@@H]1CCC[C@@H]1NC(=O)OC(C)(C)C]

Combine methyl 2-amino-4-chlorobenzoate (1.9 g, 10 mmol) and Na$_2$SO$_4$ (1.4 g, 9.8 mmol). Add tert-butyl ((1S,2R)-2-formylcyclopentyl)carbamate (2.0 g, 9.4 mmol) as a solution in 1,2-dichloroethane (30 mL). Cool the stirring solution to 0° C. and add sodium triacetoxyborohydride (4 g, 19 mmol) in portions. Add acetic acid (0.9 mL, 16 mmol) drop-wise. Allow the reaction to warm to room temperature and stir overnight. Dilute the reaction mixture with water (50 mL) and saturated aqueous sodium bicarbonate (200 mL) then extract mixture with dichloromethane (2×300 mL). Combine the organic extracts and dry over Na$_2$SO$_4$. Filter the mixture; collect the filtrate; and concentrate the filtrate. Subject the resulting residue to silica gel flash column chromatography, eluting with 0-100% EtOAc in hexanes, to provide the title compound as a white solid (1.8 g, 50%). ESMS (m/z) ($^{35}$Cl/$^{37}$Cl) 383/385 (M+H)$^+$.

PREPARATION 11

Benzyl N-[(1S,2R)-2-formylcyclohexyl]carbamate

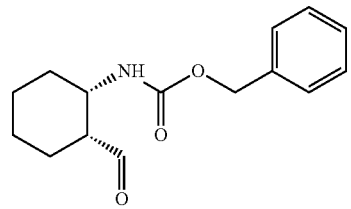 [SMILES: O=C[C@@H]1CCCC[C@@H]1NC(=O)OCc1ccccc1]

Dissolve benzyl N-[(1S,2R)-2-(hydroxymethyl)cyclohexyl]carbamate (4.312 g, 16.37 mmol) (Peter, M.; Van Der Eycken, J.; Bernath, G.; Fueloep, F. *Tet. Asymm.* 1998, 9 (13) 2339-2347) in dichloromethane (5.57 mL). Add 2,2,6,6-tetramethylpiperidine-N-oxide (0.0259 g 0.0164 mmol), and potassium bromide (0.197 g, 1.64 mmol). Cool the mixture to −10° C. Add sodium hypochlorite (0.77 M in water, 23.36 mL, 18.01 mmol) dropwise over 15 minutes and stir the mixture for 1.5 hours. Add dichloromethane (50 mL) and stir the mixture for 30 minutes. Warm to room temperature and stir the mixture overnight. Add sodium hypochlorite (0.77 M in water, 15 mL, 11.55 mmol) dropwise over 10 minutes and stir the mixture for 20 minutes. Separate the phases and extract the aqueous phase with dichloromethane (2×100 mL). Combine the organic extracts. Prepare a hydrogen chloride/potassium iodide solution by dissolving potassium iodide (1 g) in 1 M aqueous HCl (150 mL). Wash the combined organic extracts with the hydrogen chloride/potassium iodide solution, followed by 2 M aqueous sodium thiosulfate (100 mL), and then water (100 mL). Separate the phases. Dry the organic phase over MgSO$_4$; filter; collect the filtrate; and concentrate under reduced pressure. Subject the resulting crude material to silica gel flash chromatography, eluting with a gradient of 5% dichloromethane/hexanes to 75% dichloromethane/hexanes over 30 minutes, to provide the title compound as a white solid (3.563 g, 84%). ESMS (m/z) 262 (M+H)$^+$, 284 (M+Na)$^+$.

PREPARATION 12

Methyl 2-((((1S,2S)-2-(((benzyloxy)carbonyl)amino)cyclohexyl)methyl)amino)-4-chlorobenzoate

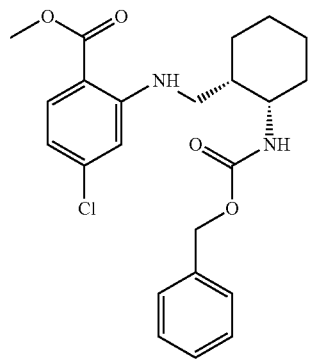 [SMILES: COC(=O)c1ccc(Cl)cc1NC[C@@H]1CCCC[C@@H]1NC(=O)OCc1ccccc1]

Dissolve methyl 2-amino-4-chlorobenzoate (0.799 g, 4.22 mmol) and benzyl N-[(1S,2R)-2-formylcyclohexyl]carbamate (1.16 g 4.44 mmol) in dichloromethane (10 mL). Add acetic acid (2 mL, 34.90 mmol) and stir for 30 minutes. Add sodium triacetoxyborohydride (1.96 g; 8.89 mmol) in one portion and stir overnight. Add ice (~15 g) to the mixture and stir until the ice melts. Extract the mixture with dichloromethane (3×50 mL). Wash the combined organic extracts with saturated aqueous sodium bicarbonate (50 mL); dry over MgSO$_4$; filter; collect the filtrate; and concentrate to dryness. Subject the crude material to silica gel flash chromatography, eluting with a gradient of hexanes to 35% EtOAc/hexanes, to provide the title compound as a colorless oil (1.15 g, 60%). ESMS (m/z) ($^{35}$Cl/$^{37}$Cl) 431/433 (M+H)$^+$.

PREPARATION 13

Methyl 2-[[(1S,2S)-2-aminocyclohexyl]methylamino]-4-chlorobenzoate

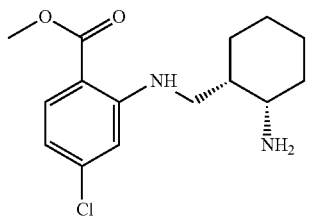 [SMILES: COC(=O)c1ccc(Cl)cc1NC[C@@H]1CCCC[C@@H]1N]

Dissolve methyl 2-(((((1S,2S)-2-(((benzyloxy)carbonyl)amino)cyclohexyl)methyl) amino)-4-chlorobenzoate (1.15 g, 2.66 mmol) in acetonitrile (20 mL). Add iodotrimethylsilane (0.42 mL, 2.92 mmol) and stir the mixture for 35 minutes. Add iodotrimethylsilane (0.42 mL, 2.92 mmol) and stir the mixture for 30 minutes. Add additional iodotrimethylsilane (0.42 mL, 2.92 mmol) and stir the mixture for 5 minutes. Dilute the mixture with EtOAc (50 mL). Wash the organics with 2 M aqueous sodium thiosulfate (20 mL). Separate the phases. Extract the aqueous phase with EtOAc (2×15 mL). Combine the organic phases and organic extracts; wash with 2 M aqueous sodium thiosulfate (20 mL); followed by saturated sodium bicarbonate (50 mL). Dry over MgSO$_4$; filter; collect the filtrate; and concentrate the filtrate. Subject the residue to silica gel flash chromatography, eluting with a gradient of dichloromethane to 10% methanol/dichloromethane over 25 minutes to provide the title compound as a white solid (0.472 g, 60%). ESMS (m/z) ($^{35}$Cl/$^{37}$Cl) 297/299 (M+H)$^+$.

PREPARATION 14

Methyl 2-(2-((1S,2S)-2-((tert-butoxycarbonyl)amino)cyclopentyl)ethyl)-4-chlorobenzoate

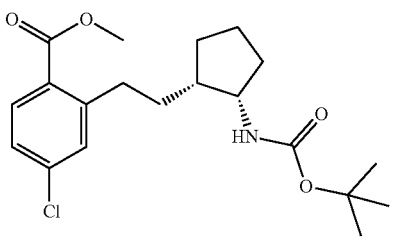 [SMILES: COC(=O)c1ccc(Cl)cc1CC[C@@H]1CCC[C@@H]1NC(=O)OC(C)(C)C]

In a PARR™ reaction vessel, suspend 5% Pt/C (1.1 g, 0.71 mmol) in EtOAc (100 mL), then add methyl 2-(2-((1S,2S)-2-((tert-butoxycarbonyl)amino)cyclopentyl)vinyl)-4-chlorobenzoate) (45 g, 26 mmol) and additional EtOAc (100 mL). Seal the vessel, purge and pressurize the mixture with hydrogen gas to 207 kPa. After 30 minutes, vent and filter the reaction mixture. Collect the filtrate. Combine this filtrate with material made by analogous procedures starting with 45 g, 5 g, and 5 g of methyl 2-(2-((1S,2S)-2-((tert-butoxycarbonyl)amino)cyclopentyl)vinyl)-4-chlorobenzoate). Remove the solvent from the combined solutions under reduced pressure to provide the title compound (99 g, 99% overall calculated on a batch-proportional basis) as a white solid. ESMS (m/z) ($^{35}$Cl/$^{37}$Cl) 404/406 (M+Na)$^+$.

PREPARATION 15

Methyl 2-(2-((1S,2S)-2-((tert-butoxycarbonyl)amino)cyclopentyl)ethyl)benzoate

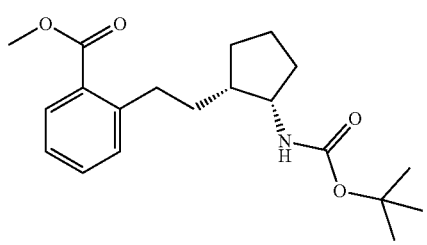 [SMILES: COC(=O)c1ccccc1CC[C@@H]1CCC[C@@H]1NC(=O)OC(C)(C)C]

Prepare the title compound essentially according to the method for Preparation 14. ESMS (m/z) 370 (M+Na)$^+$

PREPARATION 16

Ethyl 2-(2-((1S,2S)-2-((tert-butoxycarbonyl)amino)cyclopentyl)ethyl)nicotinate

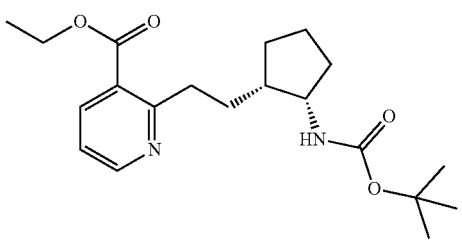 [SMILES: CCOC(=O)c1cccnc1CC[C@@H]1CCC[C@@H]1NC(=O)OC(C)(C)C]

Under a nitrogen atmosphere, treat 10% Pd/C (501 mg, 0.471 mmol) with a minimal volume of EtOAc to freely suspend the solids. Add 2-(2-((1S,2S)-2-((tert-butoxycarbonyl)amino)cyclopentyl)vinyl)nicotinate (1.7 g, 4.9 mmol) and methanol (47 mL). Seal the vessel, purge with hydrogen gas, and stir under an atmosphere of hydrogen. After 1 hour, flush the vessel with nitrogen and filter the mixture. Wash the solids with EtOAc. Collect and concentrate the filtrate to provide the title compound as a colorless oil at about 90% purity (1.76 g, 4.37 mmol, 93%). ESMS (m/z) 363 (M+H)$^+$.

PREPARATION 17

Methyl 2-(2-((1S,2S)-2-((tert-butoxycarbonyl)amino)cyclopentyl)ethyl)-4-fluorobenzoate

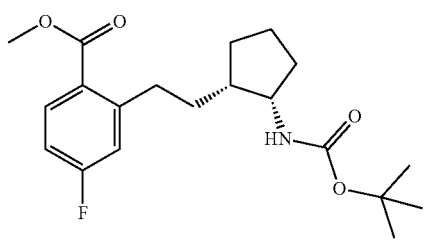 [SMILES: COC(=O)c1ccc(F)cc1CC[C@@H]1CCC[C@@H]1NC(=O)OC(C)(C)C]

To a pressure vessel, add 10% Pd/C (0.17 g) and cover the solid with methanol (50 mL). Add a solution of methyl 2-(2-((1S,2S)-2-((tert-butoxycarbonyl)amino)cyclopentyl)vinyl)-4-fluorobenzoate (1.7 g, 4.7 mmol) in methanol (50 mL). Purge the vessel with nitrogen and then hydrogen. Pressurize the vessel with hydrogen to 413 kPa and stir overnight. Depressurize and filter the mixture to remove particulates. Concentrate the filtrate to provide the title compound as a colorless oil (1.7 g, 4.7 mmol, 100%). ESMS (m/z) 388 (M+Na)$^+$.

PREPARATION 18

Methyl 2-(2-((1S,2S)-2-((tert-butoxycarbonyl)amino)cyclopentyl)ethyl)-4-methylbenzoate

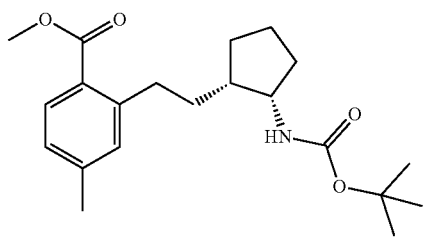 [SMILES: COC(=O)c1ccc(C)cc1CC[C@@H]1CCC[C@@H]1NC(=O)OC(C)(C)C]

Suspend 10% Pd/C (0.23 g) in a minimal volume of EtOAc, then add methyl 2-(2-((1S,2S)-2-((tert-butoxycarbonyl)amino)cyclopentyl)vinyl)-4-methylbenzoate (1.13 g, 3.14 mmol) as a solution in methanol (63 mL). Flush the vessel with hydrogen and stir under an atmosphere of hydrogen for 4 hours. In a separate pressure vessel, treat 10% palladium on carbon (0.67 g) with a minimal amount of methanol to freely suspend the solids. Add the initial reaction mixture under nitrogen to the freshly wet palladium. Flush the vessel sequentially with nitrogen and then hydrogen. Stir the solution at ambient temperature under 413 kPa hydrogen for 1 hour. Filter the reaction through diatomaceous earth, and wash the filter cake with methanol and EtOAc. Concentrate the filtrate to provide the title compound as a colorless oil (0.85 g, 2.35 mmol, 75%). ESMS (m/z) 384 (M+Na)$^+$.

PREPARATION 19

(±)-tert-Butyl N-(trans-2-ethynylcyclopentyl)carbamate

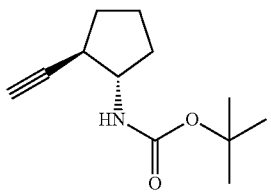

Add 1-diazo-1-dimethoxyphosphoryl-propan-2-one (1.49 mL, 6.98 mmol) to a mixture of (±)-tert-butyl N-[cis-2-formylcyclopentyl]carbamate (1.24 g, 5.81 mmol) and potassium carbonate (1.61 g, 11.63 mmol) in methanol (50 mL). Stir the mixture at room temperature for 4 hours. Concentrate the mixture under reduced pressure to provide a crude residue. Dilute the crude residue with EtOAc (100 mL), wash with a saturated aqueous solution of sodium bicarbonate (50 mL), separate the layers, and collect the organic layer. Dry the organic layer over MgSO$_4$; filter; collect the filtrate; and concentrate under reduced pressure. Subject the residue to silica gel flash chromatography, eluting with a gradient of 0% to 100% EtOAc in hexanes, to provide the title compound as a white solid (0.66 g, 54%). $^1$H NMR (400 MHz, d$_6$-DMSO) δ 6.92 (d, J=7.8 Hz, 1H), 3.71 (app quint J=7.3 Hz, 1H), 2.84 (s, 1H), 1.95-1.70 (m, 2H), 1.60-1.46 (m, 3H), 1.36 (s, 9H), 1.37-1.29 (m, 2H).

PREPARATION 20

Methyl 2-((trans-2-((tert-butoxycarbonyl)amino)cyclopentyl)ethynyl)-4-chlorobenzoate

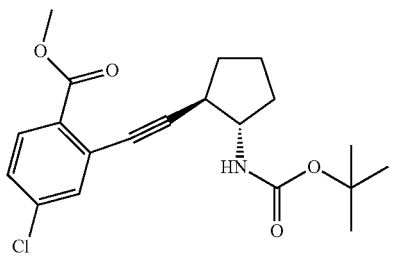 [SMILES: COC(=O)c1ccc(Cl)cc1C#C[C@H]1CCC[C@@H]1NC(=O)OC(C)(C)C]

Add diisopropylamine (0.44 mL, 3.11 mmol) to a solution of (±)-tert-butyl N-(trans-2-ethynylcyclopentyl)carbamate (0.65 g, 3.11 mmol) and methyl 4-chloro-2-iodobenzoate (1.11 g, 3.73 mmol) in tetrahydrofuran (12 mL). Purge the solution with nitrogen for 5 minutes. Add copper(I) iodide (11.8 mg, 0.062 mmol) and bis(triphenylphosphine) palladium(II) chloride (43 mg, 0.062 mmol). Stir the mixture at room temperature overnight. Quench the reaction with water (50 mL) and extract with EtOAc (3×50 mL). Combine the organic extracts; wash with brine (50 mL); collect the organic layer; dry over MgSO$_4$; filter; collect the filtrate; and concentrate under reduced pressure. Subject the resulting crude material to silica gel flash chromatography, eluting with a gradient of 0% to 50% EtOAc in hexanes, to provide

23 the title compound as a light yellow solid (0.57 g, 49%). ESMS (m/z) ($^{35}$Cl/$^{37}$Cl) 400/402 (M+Na)$^+$.

PREPARATION 21

Methyl 2-(2-(trans-2-((tert-butoxycarbonyl)amino)cyclopentyl)ethyl)-4-chlorobenzoate

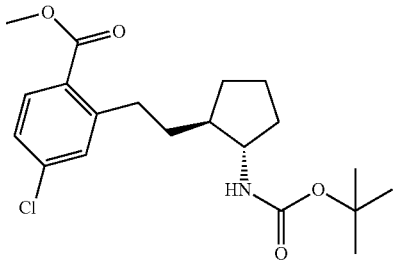 [SMILES: COC(=O)c1ccc(Cl)cc1CC[C@H]1CCC[C@@H]1NC(=O)OC(C)(C)C]

Add 10% palladium on carbon (0.40 g, 0.38 mmol) to a solution of methyl 2-((trans-2-((tert-butoxycarbonyl)amino)cyclopentyl)ethynyl)-4-chlorobenzoate (0.57 g, 1.51 mmol) in EtOAc (20 mL). Purge the solution with hydrogen and stir under an atmosphere of hydrogen for 1.5 hours. Filter the reaction mixture through diatomaceous earth. Concentrate the filtrate under reduced pressure to provide the title compound as a white solid in about 90% purity by $^1$H NMR (0.56 g, 87%). ESMS (m/z) ($^{35}$Cl/$^{37}$Cl) 404/406 (M+Na)$^+$.

24

PREPARATION 22

Methyl 2-(2-((1S,2S)-2-aminocyclopentyl)ethyl)-4-chlorobenzoate hydrochloride

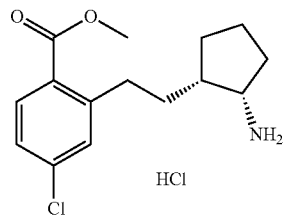 [SMILES: COC(=O)c1ccc(Cl)cc1CC[C@@H]1CCC[C@@H]1N ; Cl]

Dissolve 2-(2-((1S,2S)-2-((tert-butoxycarbonyl)amino)cyclopentyl)vinyl)-4-chlorobenzoate) (99 g, 260 mmol) in 1,4-dioxane (500 mL) and add hydrogen chloride (4.0 M solution in 1,4-dioxane, 1.0 L, 4.0 mol). Stir the mixture at room temperature overnight.

Dilute the solution with TBME (500 mL) and filter to collect the resulting white precipitate. Wash the precipitate with TBME (3×300 mL). Collect and concentrate the filtrate to provide an additional amount of a white solid. Filter the mixture to collect the white solid and wash the solid with TBME (3×300 mL). Combine both crops of white solids to provide the title compound (67.4 g, 96%). ESMS (m/z) 282 (M+H)$^+$.

Prepare the following compounds in Table 2 essentially according to procedure for Preparation 22.

TABLE 2

| Prep. No. | Chemical Name | Structure | ESMS (m/z) (M + 1)+ |
|---|---|---|---|
| 23[1,2] | Methyl 2-(2-((1S,2S)-2-aminocyclopentyl)ethyl)-4-fluorobenzoate hydrochloride | 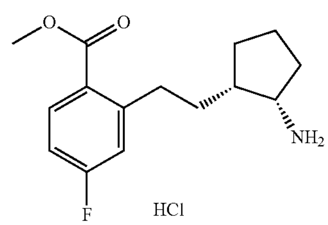 [SMILES: COC(=O)c1ccc(F)cc1CC[C@@H]1CCC[C@@H]1N ; Cl] | 266 |
| 24[1,3] | Methyl 2-(2-((1S,2S)-2-aminocyclopentyl)ethyl)-4-methylbenzoate hydrochloride | 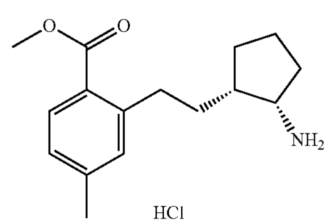 [SMILES: COC(=O)c1ccc(C)cc1CC[C@@H]1CCC[C@@H]1N ; Cl] | 262 |
| 25[3,4] | Ethyl 2-(2-((1S,2S)-2-aminocyclopentyl)ethyl)nicotinate dihydrochloride | 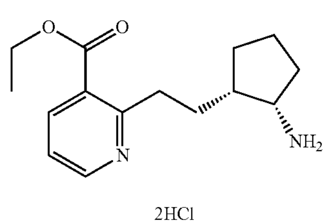 [SMILES: CCOC(=O)c1cccnc1CC[C@@H]1CCC[C@@H]1N ; "2HCl"] | 263 |

TABLE 2-continued

| Prep. No. | Chemical Name | Structure | ESMS (m/z) (M + 1)+ |
|---|---|---|---|
| 26[1,2,5] | Methyl 2-(2-((1S,2S)-2-aminocyclopentyl)ethyl)benzoate hydrochloride | 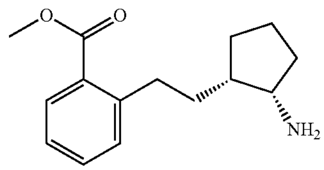 | 248 |
| 27[3,4] | Methyl 2-((((1S,2S)-2-aminocyclopentyl)methyl)amino)-4-chlorobenzoate hydrogen chloride | 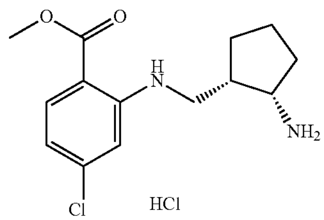 [SMILES: COC(=O)c1ccc(Cl)cc1NC[C@@H]1CCC[C@@H]1N ; Cl] | ($^{35}$Cl/$^{37}$Cl) 283/285 |
| 28[1,3] | (±)-2-((((cis)-2-Aminocyclopentyl)methyl)amino)-4-chlorobenzoate hydrogen chloride | 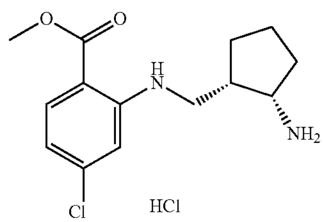 [SMILES: COC(=O)c1ccc(Cl)cc1NC[C@@H]1CCC[C@@H]1N ; Cl] | ($^{35}$Cl/$^{37}$Cl) 283/285 |
| 29[1,2] | (±)-Methyl 2-(2-(trans-2-aminocyclopentyl)ethyl)-4-chlorobenzoate hydrochloride | 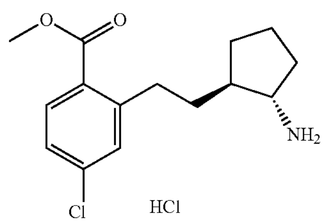 [SMILES: COC(=O)c1ccc(Cl)cc1CC[C@H]1CCC[C@@H]1N ; Cl] | ($^{35}$Cl/$^{37}$Cl) 283/285 |

[1]Suspend starting material in dichloromethane before adding 4N HCl in dioxane.
[2]Isolate title compound by precipitation with diethyl ether and filtration.
[3]Isolate title compound by concentration of crude reaction mixture.
[4]Suspend starting material directly in 4.0M HCl in dioxane.
[5]4N HCl in dioxane added to starting material at 5° C. and allowed to warm to ambient temperature.

PREPARATION 30

Methyl 2-(2-((1S,2S)-2-aminocyclopentyl)ethyl)benzoate

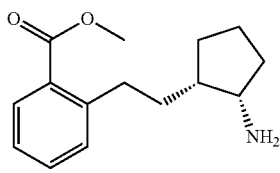 [SMILES: COC(=O)c1ccccc1CC[C@@H]1CCC[C@@H]1N]

Suspend 5% Pd/C (0.82 g, 0.4 mmol) in methanol (20 mL) in a PARR™ flask, then add methyl 2-(2-((1S,2S)-2-aminocyclopentyl)ethyl)-4-chlorobenzoate hydrochloride (8.0 g, 25 mmol), methanol (180 mL), and triethylamine (14 mL, 99 mmol) to the suspension. Seal the flask, purge, and pressurize the flask to 427 kPa with hydrogen gas. Re-pressurize the flask with hydrogen as necessary. After 3 hours, filter the reaction mixture. Concentrate the filtrate under reduced pressure. Dilute the residue with water (100 mL) and extract with dichloromethane (3×250 mL). Dry the combined organic layers over Na$_2$SO$_4$; filter; collect the filtrate; and concentrate the filtrate to provide the title compound at 97% purity (65 g, 26 mmol, 105%) as a white solid. ESMS (m/z) 248 (M+H)$^+$

PREPARATION 31

Ethyl 1-(8-methylquinolin-2-yl)piperidine-4-carboxylate

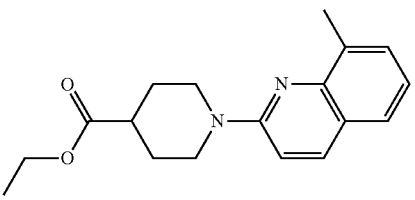 [SMILES: CCOC(=O)C1CCN(c2ccc3cccc(C)c3n2)CC1]

Combine 2-chloro-8-methyl-quinoline (50 g, 281 mmol) and ethyl piperidine-4-carboxylate (67 g, 426 mmol) in DMSO (400 mL). Add potassium carbonate (80 g, 579 mmol) and heat the mixture to 130° C., then stir overnight at 130° C. Cool the reaction mixture to room temperature, dilute with water (2.0 L), and extract with EtOAc (2×1.5 L). Combine the extracts; dry over $Na_2SO_4$; filter to remove the solids; collect the filtrate; and concentrate to provide a residue. Subject the residue to silica gel column chromatography, eluting with a gradient of 10/90 to 20/80 hexanes/TBME, to provide the title compound as a viscous, orange oil (75.5 g, 90%). ESMS (m/z) 299 (M+H)$^+$

PREPARATION 32

1-(8-Methylquinolin-2-yl)piperidine-4-carboxylic acid

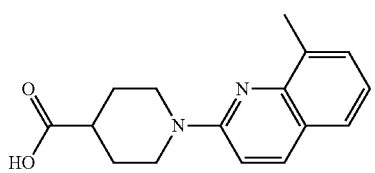 [SMILES: Cc1cccc2ccc(N3CCC(C(=O)O)CC3)nc12]

Combine ethyl 1-(8-methylquinolin-2-yl)piperidine-4-carboxylate (75.5 g, 253 mmol), tetrahydrofuran (1.0 L) and methanol (500 mL) then add 5 M aqueous sodium hydroxide (510 mL, 2.55 mol) to the solution. Stir the mixture at room temperature overnight. Concentrate the reaction mixture under reduced pressure; dilute with water (500 mL); and cool the resulting mixture to 5° C. Acidify the mixture to pH 6-7 with 5 M aqueous HCl to induce precipitation. Isolate the solid by filtration. Wash the solid thoroughly with water. Dry the solid in a vacuum oven at 40° C. overnight to provide the title compound as an off-white solid (65 g, 95%). ESMS (m/z) 271 (M+H)$^+$.

PREPARATION 33

1-(4-(Trifluoromethoxy)phenyl)piperidine-4-carboxylic acid

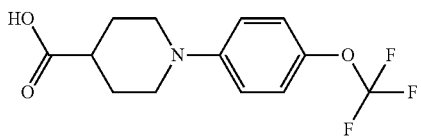 [SMILES: O=C(O)C1CCN(c2ccc(OC(F)(F)F)cc2)CC1]

Combine piperidine-4-carboxylic acid (1.00 g, 7.74 mmol), p-bromophenyl trifluoromethyl ether (1.87 g, 7.74 mmol), sodium tert-butoxide (1.86 g, 19.4 mmol, and 1,4-dioxane (77 mL). Sparge with nitrogen for 30 minutes. Add (2-dicyclohexylphosphino-2',6'-diisopropoxy-1,1'-biphenyl)[2-(2'-amino-1,1'-biphenyl)]palladium(II) methanesulfonate and reflux overnight. Cool the reaction to room temperature. Partition the mixture between water and EtOAc. Acidify the aqueous layer to pH 4 with 3 N HCl and extract with EtOAc (3×100 mL). Wash the combined organic layers with saturated aqueous NaCl; dry over $MgSO_4$; filter; collect the filtrate; and concentrate to give the title compound (1.39 g, 4.81 mmol, 62%). ESMS (m/z) 290 (M+H)$^+$.

PREPARATION 34

Methyl trans-4-hydroxycyclohexane-1-carboxylate

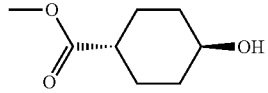

Add (trimethylsilyl)diazomethane (2.0 M in hexanes, 7.6 mL, 15 mmol) portion-wise over 15 minutes to a solution of trans-4-hydroxycyclohexane-1-carboxylic acid (2.0 g, 13.8 mmol) in anhydrous toluene (30 mL) and methanol (10 mL). Stir the mixture for ten minutes and then add acetic acid (1.0 mg, 0.017 mmol). Concentrate the mixture to provide an oil. Dry the oil under reduced pressure overnight to provide the title compound (2.14 g, 97%, H$^1$ NMR (400 MHz, d$_6$-DMSO): δ 4.54 (d, J=4.3 Hz, 1H), 3.54 (s, 3H), 3.30 (m, 1H), 2.17 (m, 1H), 1.83-1.75 (m, 4H), 1.30 (m, 2H), 1.15 (m, 2H).

PREPARATION 35 trans-4-(Benzyloxy)cyclohexane-1-carboxylic acid

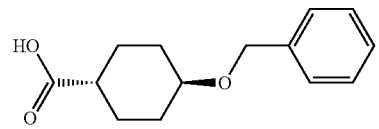 [SMILES: O=C(O)[C@H]1CC[C@H](OCc2ccccc2)CC1]

Heat a sealed mixture of methyl trans-4-hydroxycyclohexane-1-carboxylate (1.0 g, 6.3 mmol), benzylbromide (0.76 mL, 6.4 mmol), and N,N-diisopropylethylamine (2.5 mL, 14 mmol) to 150° C. for one hour. Add 1 N HCl (25 mL) to the resulting heterogeneous mixture and extract with EtOAc (3×). Dry the combined organics over $MgSO_4$ and concentrate to an orange oil. Dissolve the residual orange oil in methanol (10 mL) and tetrahydrofuran (10 mL). Add 5 N sodium hydroxide (3.0 mL). Stir the mixture overnight. Neutralize the solution with 5 N HCl (3.0 mL) and concentrate to dryness. Dissolve the resulting solids in EtOAc and water. Separate the layers, and extract the aqueous layer with EtOAc (2×). Dry the combined organics over $MgSO_4$; filter; collect the filtrate; and concentrate to provide the title compound as a solid (1.16 g, 4.95 mmol, 78%). ESMS (m/z) 233 (M−H).

PREPARATION 36

Ethyl 1-(5-fluoropyridin-2-yl)piperidine-4-carboxylate

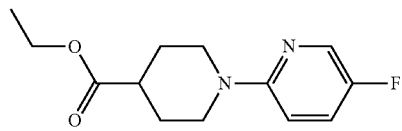

Combine ethyl piperidine 4-carboxylate (2.8 mL, 18 mmol) and 2,5-difluoropyridine (2.0 mL, 25 mmol) and pyridine (2.0 mL) in a vessel. Seal the vessel and heat to 200° C. for 1 hour. Cool the mixture to room temperature; dilute the mixture with water (15 mL) and EtOAc (50 mL); and separate the phases. Wash the EtOAc layer with saturated aqueous NaCl (15 mL). Dry the EtOAc layer over Na$_2$SO$_4$; filter; collect the filtrate; and concentrate the solution to provide a brown oil. Subject the brown oil to silica gel flash column chromatography, eluting with 90:10 to 70:30 hexanes:ethyl acetate, to provide the title compound as a colorless oil (2.32 g, 9.2 mmol, 52%). ESMS (m/z) 253 (M+H)$^+$.

PREPARATION 37

1-(5-Fluoropyridin-2-yl)piperidine-4-carboxylic acid

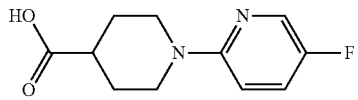

Add 2.0 M aqueous sodium hydroxide (12 mL, 24 mmol) to a solution of ethyl 1-(5-fluoro-2-pyridyl)piperidine-4-carboxylate (2.32 g, 9.2 mmol) in tetrahydrofuran (9 mL) and methanol (18 mL). Stir the solution at ambient temperature for 5 hours. Concentrate the solution and treat the residue with 5 N aqueous HCl (4.8 mL, 24 mmol) to induce precipitation. Filter the suspension; collect the white precipitate; and dry under reduced pressure to provide the title compound as a white solid (1.9 g, 84 mmol, 92%). ESMS (m/z) 225 (M+H)$^+$.

PREPARATION 38

1-(p-Tolyl)piperidine-4-carboxylic acid

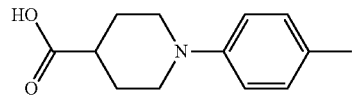 [SMILES: Cc1ccc(N2CCC(C(=O)O)CC2)cc1]

Sparge 1,4-dioxane (60 mL) with nitrogen gas for 10 minutes. Add isonipecotic acid (750 mg, 5.81 mmol), 4-bromotoluene (1.0 g, 5.85 mmol), and sodium tert-butoxide (1.4 g, 13 mmol) to the mixture. Again sparge the mixture with nitrogen. Add (2-dicyclohexylphosphino-2',6'-diisopropoxy-1,1'-biphenyl)[2-(2'-amino-1,1'-biphenyl)]palladium(II) methanesulfonate to the mixture and reflux overnight under a nitrogen atmosphere. Partition the solution between EtOAc and water. Acidify the aqueous layer with 3 N HCl to pH 4. Extract the aqueous layer with EtOAc (3×35 mL). Wash the combined organic extracts with saturated aqueous NaCl; dry over MgSO$_4$; collect the filtrate; and concentrate to provide the title compound (545 mg, 2.49 mmol, 43%). ESMS (m/z) 220 (M+H)$^+$.

PREPARATION 39

Ethyl 1-(6-(trifluoromethyl)pyridin-3-yl)piperidine-4-carboxylate

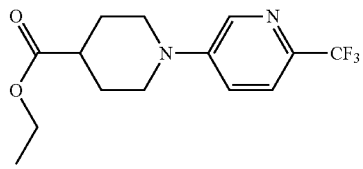 [SMILES: CCOC(=O)C1CCN(c2ccc(C(F)(F)F)nc2)CC1]

Add ethyl piperidine 4-carboxylate (0.93 mL, 6.1 mmol) and 5-fluoro-2-(trifluoromethyl)pyridine (1.0 g, 6.1 mmol). Purge the mixture with nitrogen for 5 minutes, then heat to 200° C. in a BIOTAGE™ initiator microwave for 90 minutes. Purify the reaction mixture by silica gel chromatography, eluting with a gradient of 100% hexanes to 40% EtOAc in hexanes, to give the title compound as a colorless oil (1.27 g, 4.2 mmol, 69%). ESMS (m/z) 303 (M+H)$^+$.

PREPARATION 40

1-(6-(Trifluoromethyl)pyridin-3-yl)piperidine-4-carboxylic acid

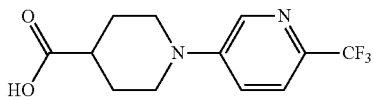

Dissolve ethyl 1-(6-(trifluoromethyl)pyridin-3-yl)piperidine-4-carboxylate (1.27 g, 4.20 mmol) in methanol (2 mL), tetrahydrofuran (10 mL), and aqueous NaOH (5 M, 1.68 mL, 8.40 mmol). Stir the mixture at room temperature overnight. Concentrate the mixture to provide to a white solid; dilute with water (20 mL); and adjust the pH to 5 with 5 N HCl. Concentrate the solution to provide a white solid. Slurry the solid in ethanol (100 mL) and filter to remove salts. Concentrate the filtrate under reduced pressure to provide the title compound as a white solid (1.10 g, 4.01 mmol, 95%). ESMS (m/z) 278 (M+H)$^+$.

PREPARATION 41

O1-tert-butyl-O4-methyl 3,3-dimethyl-2,6-dihydropyridine-1,4-dicarboxylate

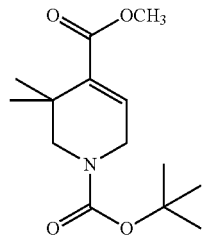 [SMILES: COC(=O)C1=CCN(C(=O)OC(C)(C)C)CC1(C)C]

Add palladium(II) acetate (4.40 g, 20.0 mmol), 1,1'-bis(diphenylphosphino)ferrocene (13.3 g, 22.8 mmol), tert-butyl 3,3-dimethyl-4-(trifluoromethylsulfonyloxy)-2,6-dihydropyridine-1-carboxylate (72.0 g, 150 mmol), anhydrous acetonitrile (850 mL), anhydrous methanol (570 mL), and triethylamine (36.0 mL, 245 mmol) to a 2-L PARR™ autoclave fitted with a mechanical stirrer. Seal the reactor; purge; and pressurize with carbon monoxide to 689 kPa. Heat the mixture to 65° C. for 2.25 h; then cool the mixture to room temperature; and carefully vent the reaction vessel (Caution! Poison gas!) Concentrate under reduced pressure. Combine this material with five other batches of material prepared essentially by the same procedure on similar scales and subject the combined material to flash chromatography on silica gel, eluting with a gradient of 0% to 20% TBME in hexanes, to provide the title compound as a yellow oil in about 83% purity by mass (260 g, 88%). ESMS (m/z) 214 (M−t-Bu+2H)$^+$.

PREPARATION 42

O1-tert-Butyl-O4-methyl
3,3-dimethylpiperidine-1,4-dicarboxylate

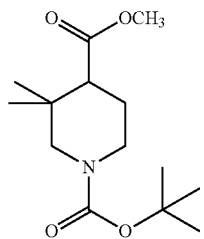 [SMILES: COC(=O)C1CCN(C(=O)OC(C)(C)C)CC1(C)C]

Suspend palladium (10 wt % on carbon, 5.4 g, 5.1 mmol) in methanol (700 mL), then add a solution of O1-tert-butyl-O4-methyl 3,3-dimethyl-2,6-dihydropyridine-1,4-dicarboxylate (130 g, 396 mmol) in methanol (700 mL). Seal the mixture in a vessel; and sequentially purge the vessel with nitrogen then hydrogen. Pressurize the vessel to 414 kPa of hydrogen and stir at room temperature for 1.5 hours. Release the pressure and filter the mixture to remove catalyst. Combine the filtrate with that from another reaction prepared by a similar procedure and remove the volatile solvents under reduced pressure to provide the title compound as a yellow oil in about 85% purity by mass (240 g, 95%). ESMS (m/z) 216 (M−t-Bu+2H)$^+$.

PREPARATION 43

Methyl 3,3-dimethylpiperidine-4-carboxylate hydrochloride

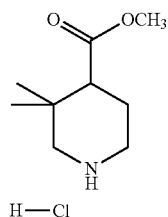

Add HCl (4.0 M solution in 1,4-dioxane, 2.0 L, 8.0 mol) to a solution of O1-tert-butyl-O4-methyl 3,3-dimethylpiperidine-1,4-dicarboxylate (240 g, 752 mmol) in 1,4-dioxane (500 mL). Stir the resulting mixture at room temperature overnight, then concentrate under reduced pressure. Dilute the residue with TBME (500 mL) and isolate the solids by filtration. Rinse the filter cake with TBME (2×400 mL) and dry the solids in a 35° C. vacuum oven overnight to provide the title compound as a white solid (144 g, 92%). ESMS (m/z) 172 (M+H)$^+$.

PREPARATION 44

(−)-Methyl (4S)-3,3-dimethyl-1-(8-methyl-2-quinolyl)piperidine-4-carboxylate

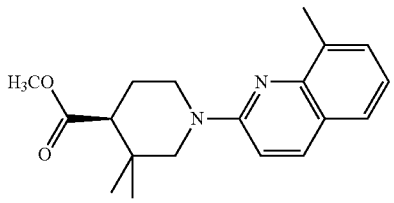 [SMILES: COC(=O)[C@H]1CCN(c2ccc3cccc(C)c3n2)CC1(C)C]

Combine methyl 3,3-dimethylpiperidine-4-carboxylate hydrochloride (144 g, 693 mmol), 2-chloro-8-methylquinoline (125 g, 704 mmol), DMSO (1.4 L), and K$_2$CO$_3$ (210 g, 1.52 mol). Stir the resulting mixture at 131±1° C. overnight. Cool the mixture to room temperature, filter to remove the solids; dilute with water (2 L); and extract with EtOAc (2×3 L). Wash the combined organic extracts with water (3×1.5 L); dry over Na$_2$SO$_4$; filter; collect the filtrate; and concentrate under reduced pressure. Subject the resulting crude material to flash chromatography on silica gel, eluting with a gradient of 25% to 30% (10% TBME in DCM) in hexanes, to provide the title compound as a racimate. Dissolve this material in methanol (7.5 L) and filter the solution. Label the filtrate as "Solution A." Subject the material to chiral SFC (Chiralpak OJ-H, 50 mm×250 mm×5 μm) using 15% (0.2% dimethylethylamine in i-PrOH) in CO$_2$ as the mobile phase at a flow rate of 400 g/min, by injecting 5 mL of Solution A every 95 seconds until all of the material has been consumed. For each injection, collect the first fraction to elute ($t_R$=2.57 min by SFC Method 1) and discard the second ($t_R$=3.17 min by SFC Method 1). Combine the collected fractions with those from an isolated from a previous reaction and remove the volatile to provide 98 g of crude methyl 3,3-dimethylpiperidine-4-carboxylate hydrochloride. Recrystallize the material from hot ethanol (1.38 L); isolate the crystals by filtration; and dry in a 40° C. vacuum oven overnight to provide the title compound as a white crystalline solid (156 g, 43% yield on a batch-proportional basis). ESMS (m/z) 313 (M+H)$^+$, $[\alpha]^{20}_D$ −45° (c 0.21, CH$_2$Cl$_2$). ee=>99% as determined by SFC Method 1. For SFC Method 1: Analyses are carried out on a Daicel ChiralPak OJ-H column (100 mm length, 4.6 mm internal diameter, 5 μm particle size). The mobile phase used is: 8% (20 mM NH$_3$ in i-PrOH) and 92% CO$_{2(scf)}$ at a pressure of 100 bar. The run is performed at a temperature of 35° C. and a flow rate of 3 mL/minute. The UV (DAD) acquisition is performed at a wavelength of 220 nm.

PREPARATION 45

(−)-(4S)-3,3-Dimethyl-1-(8-methyl-2-quinolyl)piperidine-4-carboxylic acid

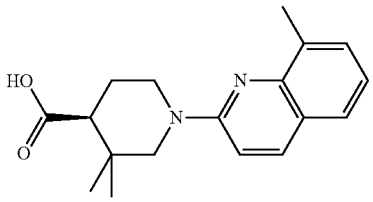 [SMILES: Cc1cccc2ccc(N3CC[C@H](C(=O)O)C(C)(C)C3)nc12]

Treat methyl (4S)-3,3-dimethyl-1-(8-methyl-2-quinolyl)piperidine-4-carboxylate (154 g, 493 mmol) with sulfuric acid (10% v/v in water, 2.31 L, 2.75 mol). Heat the mixture to reflux with stirring overnight. Cool the mixture to room temperature then add NaOH (50 wt % in water) until the pH reaches 13. Add TBME (500 mL) to give a triphasic mixture. From top to bottom, label the layers "Layer A," "Layer B," and "Layer C." Remove Layer C. To Layers A and B, add water (600 mL) then set aside the organic layer. Combine the aqueous layer with Layer C. Extract Layer C with TBME (500 mL) and set aside the organic layer. Add HCl (5.0 M in water) to Layer C until the pH reaches 6.5. Extract Layer C with TBME (2×400 mL). Combine all the organic extracts; dry over MgSO$_4$; filter; collect the filtrate; and concentrate under reduced pressure to provide the title compound as a white solid in 96% purity (145 g, 95%). ESMS (m/z) 299 (M+H)$^+$, $[\alpha]^{20}_D$ −59.6° (c 3.12, CH$_3$OH).

PREPARATION 46

Methyl 2-(2-((1S,2S)-2-(1-(8-methylquinolin-2-yl)piperidine-4-carboxamido)cyclopentyl)ethyl)benzoate

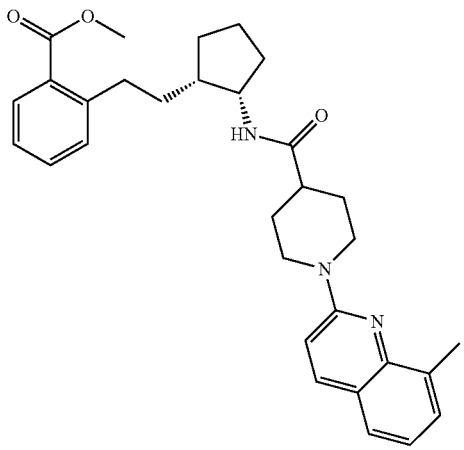 [SMILES: COC(=O)c1ccccc1CC[C@@H]1CCC[C@@H]1NC(=O)C1CCN(c2ccc3cccc(C)c3n2)CC1]

Dissolve methyl 2-(2-((1S,2S)-2-aminocyclopentyl)ethyl)benzoate (6.5 g, 26 mmol, 97% purity) and 1-(8-methylquinolin-2-yl)piperidine-4-carboxylic acid (7.8 g, 29 mmol) in dichloromethane (350 mL). Cool the mixture to 0° C. and add diisopropylethylamine (10 mL, 57 mmol). Add 1-propanephosphonic acid cyclic anhydride (50 wt % in EtOAc 25 mL, 41.6 mmol) at a rate to maintain the internal temperature of the reaction between 0° C. and 4° C. Allow the reaction to warm to room temperature overnight. Carefully pour the mixture into aqueous NaHCO$_3$ (1.0 L). Separate the layers and extract the aqueous layer with dichloromethane (500 mL). Combine the organic layers; wash the combined organic layers with saturated, aqueous NaCl (200 mL); dry over Na$_2$SO$_4$; filter; collect the filtrate; and concentrate the filtrate to provide a residue. Subject the residue to silica gel flash column chromatography, eluting with a gradient of 20 to 29% TBME in a 1:1 mixture of dichloromethane and hexanes. Repurify mixed fractions by silica gel flash column chromatography, eluting with a gradient of dichloromethane to 25% TBME in dichloromethane to give the title compound (10.8 g, 84%). ESMS (m/z) 500 (M+H)$^+$

PREPARATION 47

Methyl 4-fluoro-2-(2-((1S,2S)-2-(1-(4-(trifluoromethyl)phenyl)piperidine-4-carboxamido)cyclopentyl)ethyl)benzoate

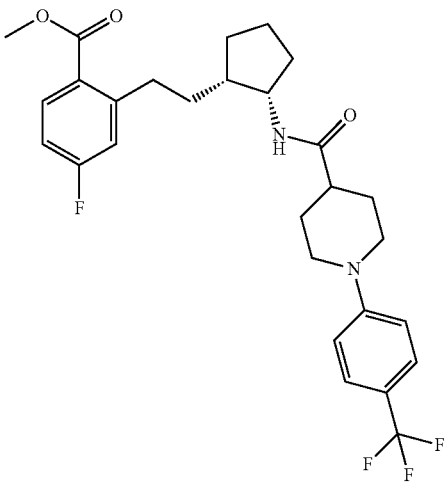 [SMILES: COC(=O)c1ccc(F)cc1CC[C@@H]1CCC[C@@H]1NC(=O)C1CCN(c2ccc(C(F)(F)F)cc2)CC1]

Combine methyl 2-(2-((1S,2S)-2-aminocyclopentyl)ethyl)-4-fluorobenzoate hydrochloride (0.15 g, 0.50 mmol), 1-(4-(trifluoromethyl)phenyl)piperidine-4-carboxylic acid (0.14 g, 0.52 mmol), and EtOAc (5 mL). Add diisopropylethylamine (0.26 mL, 1.5 mmol) and 1-propanephosphonic acid cyclic anhydride (50% solution in EtOAc, 0.51 mL, 0.99 mmol). Stir the reaction at room temperature overnight. Dilute the reaction with saturated aqueous NaHCO$_3$ and stir for thirty minutes. Dilute the organic layer with EtOAc (10 mL) and partition. Wash the organics again with saturated aqueous NaHCO$_3$; dry over MgSO$_4$; filter collect the filtrate; and concentrate to a white solid. Subject the residue to silica gel flash column chromatography eluting with a gradient of 10% to 50% EtOAc in dichloromethane to provide the title compound (0.127 mg, 0.24 mmol, 49%). ESMS (m/z) 521 (M+H)$^+$.

PREPARATION 48

Methyl 4-methyl-2-(2-((1S,2S)-2-(1-(4-(trifluoromethyl)phenyl)piperidine-4-carboxamido)cyclopentyl)ethyl)benzoate

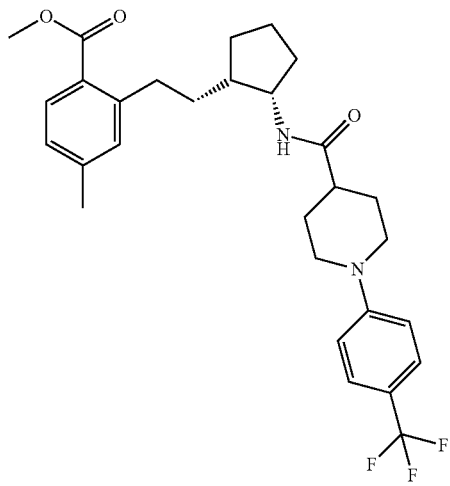

Prepare the title compound essentially according the procedure described for Preparation 48. ESMS (m/z) (M+1)+ 517

PREPARATION 49

Methyl 4-chloro-2-(2-((1S,2S)-2-(1-(p-tolyl)piperidine-4-carboxamido)cyclopentyl)ethyl)benzoate

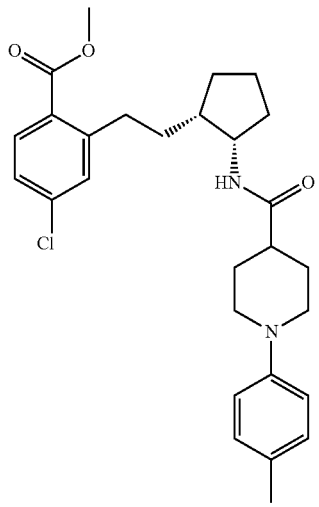 [SMILES: COC(=O)c1ccc(Cl)cc1CC[C@@H]1CCC[C@@H]1NC(=O)C1CCN(c2ccc(C)cc2)CC1]

Combine methyl 2-(2-((1S,2S)-2-aminocyclopentyl)ethyl)-4-chlorobenzoate hydrochloride (100 mg, 0.314 mmol), 1-(p-tolyl)piperidine-4-carboxylic acid (75 mg, 0.342 mmol), and 1-hydroxybenzotriazole hydrate (12 mg, 0.087 mmol) in dichloromethane (5 mL) and triethylamine (0.150 mL, 1.08 mmol) to provide a slurry. Add EDCI (100 mg, 0.52 mmol). Stir the mixture at room temperature overnight. Subject the mixture to silica gel flash column chromatography, eluting with 50/50 EtOAc/heptane, to provide the title compound (95 mg, 0.196 mmol, 62%). ESMS (m/z) 483 (M+H)+ as a white solid.

Prepare the following compounds in Table 3 essentially according to the procedure listed above for Preparation 49.

TABLE 3

| Prep. No. | Chemical Name | Structure | ESMS (m/z) (M + 1)+ |
|---|---|---|---|
| 50[1] | Methyl 4-chloro-2-(2-((1S,2S)-2-(1-(5-fluoropyridin-2-yl)piperidine-4-carboxamido)cyclopentyl)ethyl)benzoate | 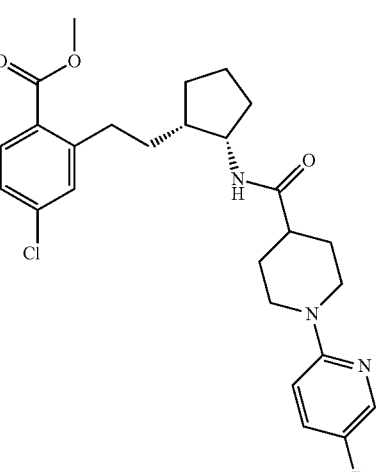 | 488 |

TABLE 3-continued

| Prep. No. | Chemical Name | Structure | ESMS (m/z) (M + 1)+ |
|---|---|---|---|
| 51 | Methyl 2-(2-((1S,2S)-2-((trans)-4-(benzyloxy)cyclohexane-1-carboxamido)cyclopentyl)ethyl)-4-chlorobenzoate | 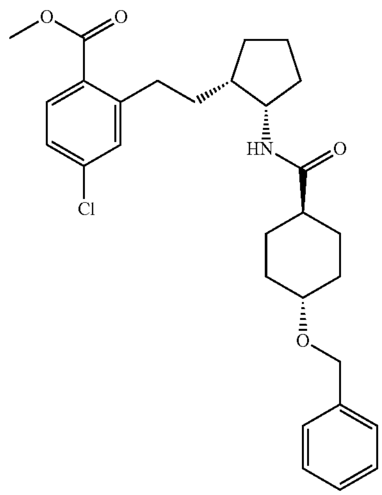 [SMILES: COC(=O)c1ccc(Cl)cc1CC[C@@H]1CCC[C@@H]1NC(=O)[C@H]1CC[C@H](OCc2ccccc2)CC1] | 498 |
| 52[3] | Methyl 2-(2-((1S,2S)-2-(1-(4-(trifluoromethoxy)phenyl)piperidine-4-carboxamido)cyclopentyl)ethyl)benzoate | 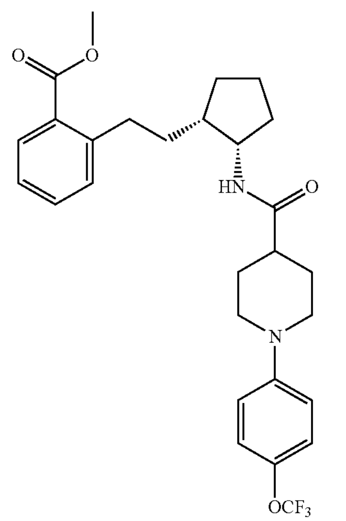 | 519 |
| 53[2] | Methyl 2-(2-((1S,2S)-2-(1-(5-(trifluoromethyl)pyridin-2-yl)piperidine-4-carboxamido)cyclopentyl)ethyl)benzoate | 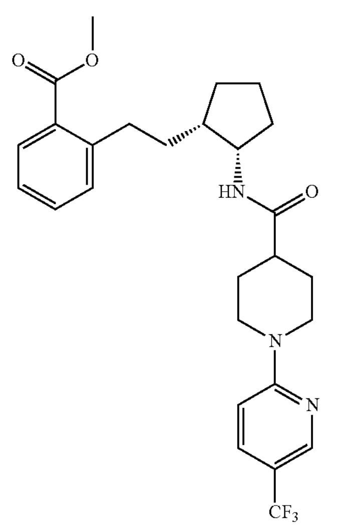 [SMILES: COC(=O)c1ccccc1CC[C@@H]1CCC[C@@H]1NC(=O)C1CCN(c2ccc(C(F)(F)F)cn2)CC1] | 504 |

[1]Chromatography elution with a gradient of 95:5 to 50:50 hexanes:ethyl acetate.
[2]Chromatography elution with a gradient of 100:0 to 50:50 hexanes:ethyl acetate.

PREPARATION 54

Methyl 2-(2-((1S,2S)-2-(1-(4-(trifluoromethyl)phenyl)piperidine-4-carboxamido)cyclopentyl)ethyl)benzoate

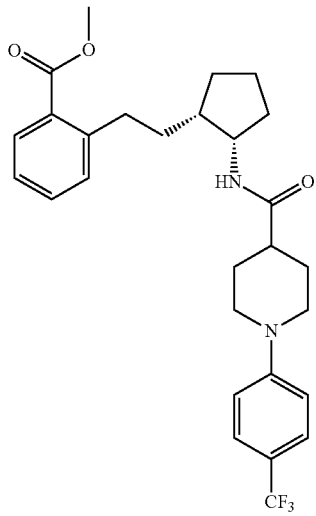 [SMILES: COC(=O)c1ccccc1CC[C@@H]1CCC[C@@H]1NC(=O)C1CCN(c2ccc(C(F)(F)F)cc2)CC1]

Combine methyl 2-(2-((1S,2S)-2-aminocyclopentyl)ethyl) benzoate hydrochloride (0.25 g, 0.88 mmol), 1-(4-(trifluoromethyl)phenyl) piperidine-4-carboxylic acid (0.25 g, 0.88 mmol), and dimethylformamide (4.4 mL). Add BOP (0.52 g, 1.1 mmol) and triethylamine (0.43 mL, 3.1 mmol). Stir the mixture at room temperature overnight. Dilute with water and extract with EtOAc (3×20 mL). Wash the combined organics with saturated aqueous sodium chloride; and dry over $MgSO_4$; filter; collect the filtrate; and concentrate under reduced pressure. Subject the concentrated residue to silica gel flash column chromatography, eluting with a gradient of 10/90 to 75/25 EtOAc/hexanes, to provide the title compound (0.3 g, 70%). ESMS (m/z) 503 (M+H)$^+$.

Prepare the following compounds in Table 4 essentially according to the procedure listed above for Preparation 54.

TABLE 4

| Prep. No. | Chemical Name | Structure | ESM (m/z) (M + 1)$^+$ |
|---|---|---|---|
| 55[1] | Methyl 4-chloro-2-(2-((1S,2S)-2-(1-(4-(trifluoromethyl)phenyl) piperidine-4-carboxamido)cyclopentyl)ethyl) benzoate | 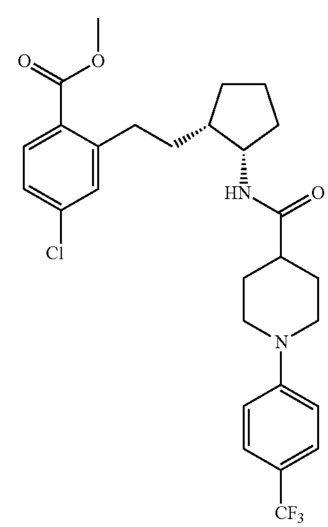 | ($^{35}$Cl/$^{37}$Cl) 537/539 |

TABLE 4-continued

| Prep. No. | Chemical Name | Structure | ESM (m/z) (M + 1)+ |
|---|---|---|---|
| 56[2,3] | Methyl 4-chloro-2-(2-((1S,2S)-2-(1-(6-(trifluoromethyl)pyridin-3-yl)piperidine-4-carboxamido)cyclopentyl)ethyl)benzoate | 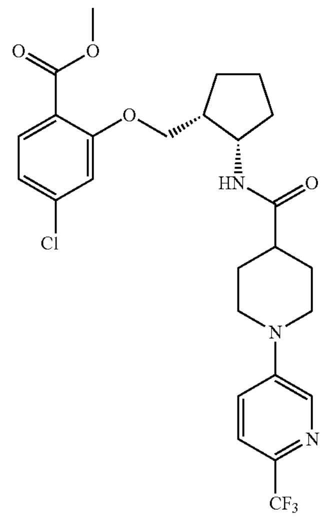 [SMILES: COC(=O)c1ccc(Cl)cc1OC[C@@H]1CCC[C@@H]1NC(=O)C1CCN(c2ccc(C(F)(F)F)nc2)CC1] | ($^{35}$Cl/$^{37}$Cl) 538/540 |
| 57[4] | Methyl 4-chloro-2-(2-((1S,2S)-2-((S)-3,3-dimethyl-1-(8-methylquinolin-2-yl)piperidine-4-carboxamido)cyclopentyl)ethyl)benzoate | 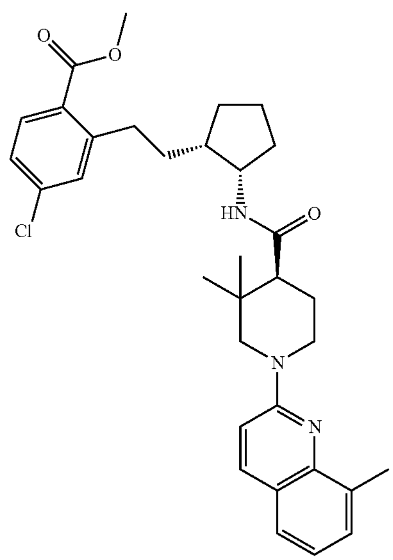 [SMILES: COC(=O)c1ccc(Cl)cc1CC[C@@H]1CCC[C@@H]1NC(=O)[C@H]1CCN(c2ccc3cccc(C)c3n2)CC1(C)C] | ($^{35}$Cl/$^{37}$Cl) 562/564 |
| 58[2,5] | Ethyl 2-(2-((1S,2S)-2-(1-(4-(trifluoromethyl)phenyl)piperidine-4-carboxamido)cyclopentyl)ethyl)nicotinate | 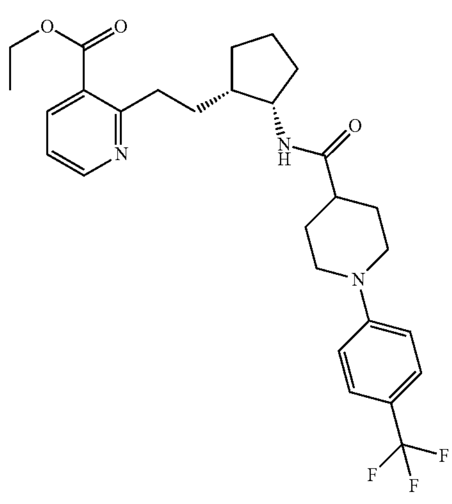 [SMILES: CCOC(=O)c1cccnc1CC[C@@H]1CCC[C@@H]1NC(=O)C1CCN(c2ccc(C(F)(F)F)cc2)CC1] | 518 |

TABLE 4-continued
| Prep. No. | Chemical Name | Structure | ESM (m/z) (M + 1)+ |
|---|---|---|---|
| 59[6] | Methyl 4-chloro-2-(((((1S,2S)-2-(1-(4-(trifluoromethyl)phenyl)piperidine-4-carboxamido)cyclopentyl)methyl)amino)benzoate | 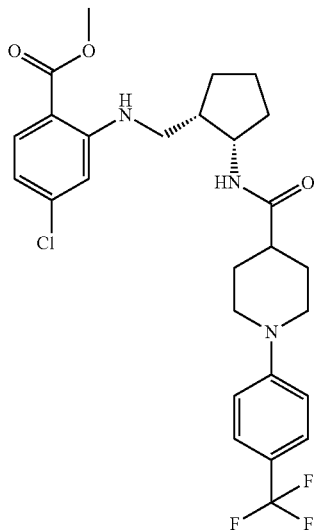 [SMILES: COC(=O)c1ccc(Cl)cc1NC[C@@H]1CCC[C@@H]1NC(=O)C1CCN(c2ccc(C(F)(F)F)cc2)CC1] | ($^{35}$Cl/$^{37}$Cl) 537/539 |
| 60[2,7] | Methyl 2-[[(1S,2S)-2-aminocyclohexyl]methylamino]-4-chlorobenzoate | 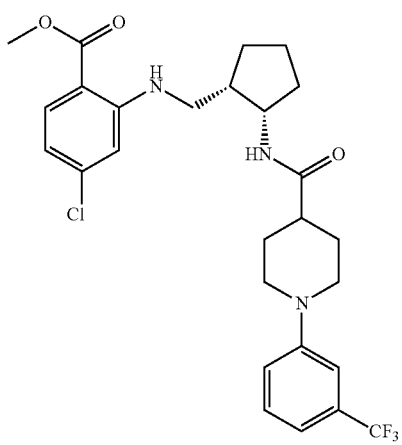 [SMILES: COC(=O)c1ccc(Cl)cc1NC[C@@H]1CCC[C@@H]1NC(=O)C1CCN(c2cccc(C(F)(F)F)c2)CC1] | ($^{35}$Cl/$^{37}$Cl) 552/554 |

| Prep. No. | Chemical Name | Structure | ESM (m/z) (M + 1)+ |
|---|---|---|---|
| 61[6] | (±)-Methyl 4-chloro-2-(2-(trans-2-(1-(4-(trifluoromethyl)phenyl)piperidine-4-carboxamido)cyclopentyl)ethyl)benzoate | 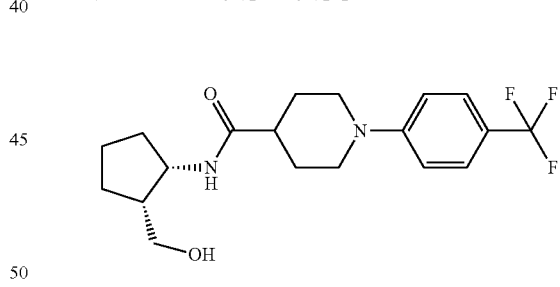 | ([35]Cl/[37]Cl) 536/538 |

[1]Perform chromatography using a gradient of 0:100 to 25:75 dichloromethane:EtOAc.
[2]Use diisopropylethylamine as the base.
[3]Perform chromatography using a gradient of 10:90 to 20:80 hexanes:EtOAc.
[4]Perform chromatography using a gradient of 10:90 to 0:100 hexanes:EtOAc.
[5]Perform chromatography using a gradient of 0:100 to 50:50 dichloromethane:ethyl acetate.
[6]Perform chromatography using a gradient of 10:90 to 0:100 hexanes: EtOAc. After silica gel flash column chromatography, purify the residue by reverse phase chromatography, eluting with acetonitrile and water modified with 0.1% formic acid to give the title compound.
[7]Purify the crude residue twice by column chromatography using 100:0 to 85:15 dichloromethane:ethyl acetate as the eluent. Purify the resulting residue again by column chromatography using a gradient to 100:0 to 10:90 dichloromethane:EtOAc.

PREPARATION 62

((1R,2S)-2-Aminocyclopentane)methanol hydrochloride

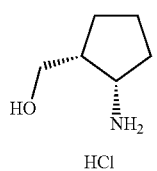

Combine tert-butyl ((1S,2R)-2-(hydroxymethyl)cyclopentyl)carbamate (1.15 g, 5.34 mmol) and HCl (4.0 M in dioxane, 62 mL). Stir the solution at room temperature for two hours and then concentrate under reduced pressure to provide the title compound as a white solid (802 mg, 5.29 mmol). $^1$H NMR (400 MHz, d$_6$-DMSO) δ 3.00 (dd, J=11.2, 4.9 Hz, 1H), 2.94-2.84 (m, 2H), 1.61-1.51 (m, 1H), 1.49-1.29 (m, 1H), 1.14-0.72 (m, 5H).

PREPARATION 63

N-((1S,2R)-2-(Hydroxymethyl)cyclopentyl)-1-(4-(trifluoromethyl)phenyl)piperidine-4-carboxamide Dissolve ((1R,2S)-2-aminocyclopentyl)methanol hydrochloride (200 mg, 1.3 mmol) in dimethylformamide (6.6 mL) and add 1-(4-(trifluoromethyl)phenyl)piperidine-4-carboxylic acid (360 mg, 1.32 mmol), diisopropylethylamine (1.38 mL, 7.91 mmol) and O-(7-Azobenzotriazol-1-yl)-N,N,N',N'-tetramethyluronium hexafluorophosphate (601 mg, 1.58 mmol). Stir the mixture at ambient temperature overnight. Dilute the mixture with EtOAc and wash the resulting mixture sequentially with 1 N aqueous HCl, saturated aqueous NaHCO$_3$, 5% aqueous LiCl, and saturated aqueous NaCl. Dry the organic phase over Na$_2$SO$_4$; filter, collect the filtrate; and concentrate under reduced pressure to provide the title compound as a tan solid (600 mg, 98%). ESMS (m/z) 371 (M+H)+.

EXAMPLE 1

2-(2-((1S,2S)-2-(1-(8-Methylquinolin-2-yl)piperidine-4-carboxamido)cyclopentyl)ethyl)benzoic acid

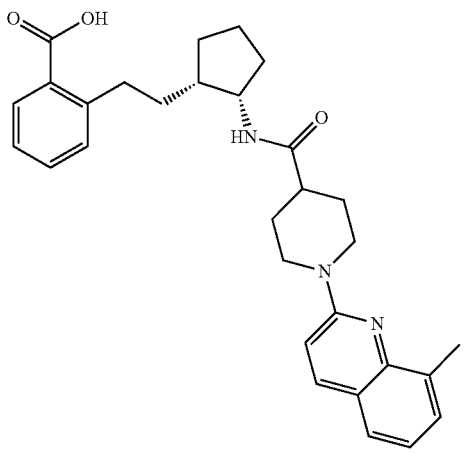 [SMILES: Cc1cccc2ccc(N3CCC(C(=O)N[C@H]4CCC[C@H]4CCc4ccccc4C(=O)O)CC3)nc12]

Dissolve methyl 2-(2-((1S,2S)-2-(1-(8-methylquinolin-2-yl)piperidine-4-carboxamido)cyclopentyl)ethyl)benzoate (10.7 g, 21.4 mmol) in tetrahydrofuran (150 mL) and methanol (100 mL). Drop-wise add 5 M aqueous sodium hydroxide (45 mL, 225 mmol) to the mixture. Stir the reaction mixture at room temperature overnight. Warm the reaction mixture to 35° C. and stir for an additional 8 hours. Cool the mixture to room temperature and concentrate it under reduced pressure. Dilute the residue with water (500 mL) and acidify the resulting mixture to pH 6-7 with 1 N HCl. Isolate the precipitated solid by filtration and wash the filter cake thoroughly with water. Dry the solid to provide the title compound as an off-white solid (10 g, 96%). ESMS (m/z) 486 (M+H)$^+$

EXAMPLE 2

2-(2-((1S,2S)-2-(1-(4-(Trifluoromethoxy)phenyl)piperidine-4-carboxamido)cyclopentyl)ethyl)benzoic acid

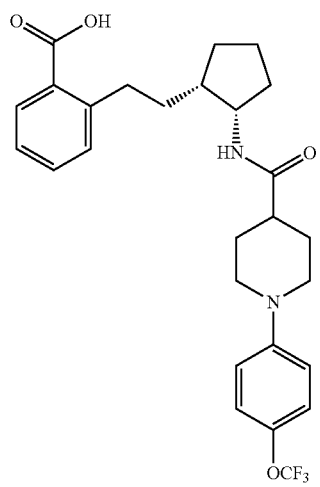 [SMILES: O=C(O)c1ccccc1CC[C@@H]1CCC[C@@H]1NC(=O)C1CCN(c2ccc(OC(F)(F)F)cc2)CC1]

Add 2 N aqueous sodium hydroxide (0.70 mL, 1.4 mmol) to a solution of methyl 2-(2-((1S,2S)-2-(1-(4-(trifluoromethoxy)phenyl)piperidine-4-carboxamido)cyclopentyl)ethyl) benzoate (135 mg, 0.260 mmol) in methanol (2.0 mL) and tetrahydrofuran (2.0 mL). Heat the mixture to 70° C. After three hours, add 2 N aqueous sodium hydroxide (0.70 mL, 1.4 mmol). Heat the mixture at 70° C. for an additional hour. Add 5 N aqueous HCl (0.56 mL). Concentrate the mixture to dryness. Triturate the solids with a small amount of methanol and then add water. Collect the solids by vacuum filtration to provide the title compound as a white solid in 93% purity by LCMS (114 mg, 0.20 mmol, 81%). ESMS (m/z) 505 (M+H)$^+$.

EXAMPLE 3

2-(2-((1S,2S)-2-(1-(5-(Trifluoromethyl)pyridin-2-yl)piperidine-4-carboxamido)cyclopentyl)ethyl)benzoic acid

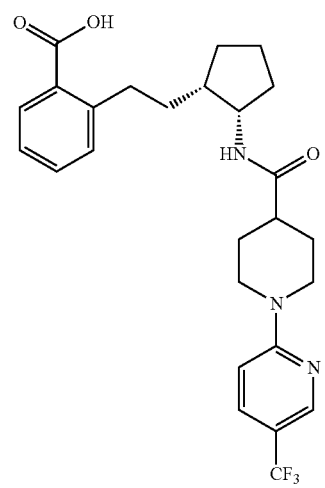 [SMILES: O=C(O)c1ccccc1CC[C@@H]1CCC[C@@H]1NC(=O)C1CCN(c2ccc(C(F)(F)F)cn2)CC1]

Add 5 N aqueous sodium hydroxide (2 mL, 10 mmol) to a solution of methyl 2-(2-((1S,2S)-2-(1-(5-(trifluoromethyl)pyridin-2-yl)piperidine-4-carboxamido)cyclopentyl)ethyl) benzoate (700 mg, 1.39 mmol) in methanol (10 mL) and tetrahydrofuran (10 mL). Heat the mixture to 70° C. After three hours, add 5 N aqueous sodium hydroxide (2 mL, 10 mmol). Heat the reaction at 70° C. for an additional two hours. Add 5 N HCl (4 mL) and concentrate to dryness. Triturate the solids with a small amount of methanol and then add water. Collect the solids by vacuum filtration to provide the title compound as a white solid (551 mg, 1.13 mmol, 82%). ESMS (m/z) 490 (M+H)$^+$.

EXAMPLE 4

2-(2-((1S,2S)-2-(1-(4-(Trifluoromethyl)phenyl)piperidine-4-carboxamido)cyclopentyl)ethyl)benzoic acid

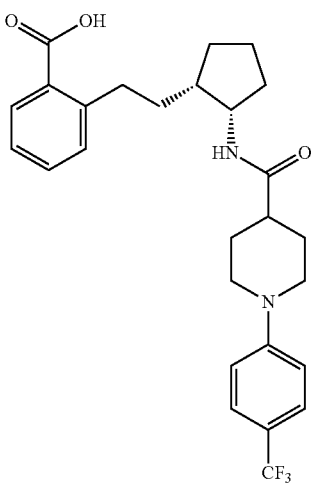 [SMILES: O=C(O)c1ccccc1CC[C@@H]1CCC[C@@H]1NC(=O)C1CCN(c2ccc(C(F)(F)F)cc2)CC1]

Dissolve methyl 2-(2-((1S,2S)-2-(1-(4-(trifluoromethyl)phenyl)piperidine-4-carboxamido)cyclopentyl)ethyl)benzoate (0.3 g, 0.6 mmol) in methanol (3 mL) and tetrahydrofuran (10 mL). Add lithium hydroxide (0.5 M in water, 5 mL, 2 mmol). Heat the mixture to 45° C. overnight. Cool the mixture to room temperature and remove the volatiles on a rotary evaporator. Acidify the solution with 5 N HCl to induce precipitation. Collect the precipitate; wash with water; and dry under vacuum to provide the title compound (0.31 g, 0.63 mmol, 100%). ESMS (m/z) 489 (M+H)$^+$.

EXAMPLE 5

2-(2-((1S,2S)-2-((trans)-4-(Benzyloxy)cyclohexane-1-carboxamido)cyclopentyl)ethyl)-4-chlorobenzoic acid

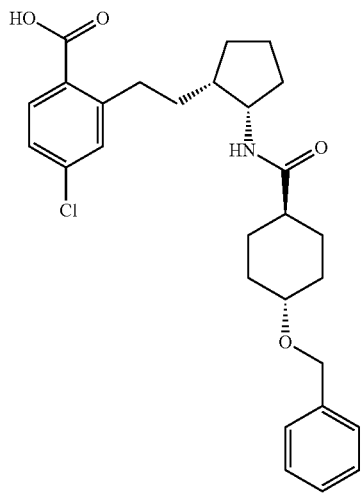 [SMILES: O=C(O)c1ccc(Cl)cc1CC[C@@H]1CCC[C@@H]1NC(=O)[C@H]1CC[C@H](OCc2ccccc2)CC1]

Add 4 N aqueous sodium hydroxide (2.0 mL) to a solution of methyl 2-(2-((1S,2S)-2-((trans)-4-(benzyloxy)cyclohexane-1-carboxamido)cyclopentyl)ethyl)-4-chlorobenzoate (518 mg, 1.04 mmol) in methanol (5 mL) and tetrahydrofuran (4 mL). Heat the mixture to 70° C. After 3 hours, add 5 N aqueous HCl (2 mL) and concentrate to dryness. Triturate the solids with a small amount of methanol and then add water. Collect the solids by filtration to provide the title compound as a white solid (425 mg, 0.878 mmol, 84%). ESMS (m/z) ($^{35}$Cl/$^{37}$Cl) 484/486 (M+H)$^+$.

EXAMPLE 6

4-Chloro-2-(2-((1S,2S)-2-(1-(5-fluoropyridin-2-yl)piperidine-4-carboxamido)cyclopentyl)ethyl)benzoic acid

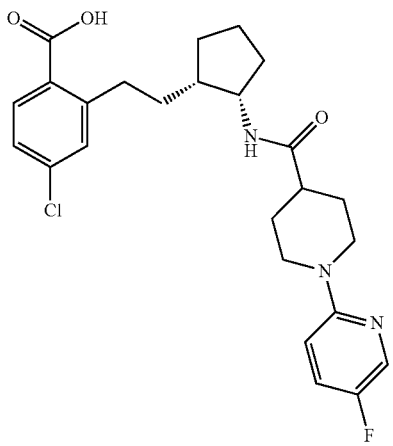 [SMILES: O=C(O)c1ccc(Cl)cc1CC[C@@H]1CCC[C@@H]1NC(=O)C1CCN(c2ccc(F)cn2)CC1]

Add 2.0 M aqueous sodium hydroxide (0.4 mL, 0.8 mmol) to a solution of methyl 4-chloro-2-(2-((1S,2S)-2-(1-(5-fluoropyridin-2-yl)piperidine-4-carboxamido)cyclopentyl)ethyl) benzoate (80 mg, 0.16 mmol) in tetrahydrofuran (1.0 mL) and methanol (2 mL). Heat the mixture to 52° C. for 6.5 hours. Cool the reaction mixture and concentrate under reduced pressure. Treat the mixture with ice and acidify to pH 4 using 1.0 N HCl. Dilute the mixture with saturated aqueous NaCl (15 mL) and extract with EtOAc (20 mL). Dry the organic extract over Na$_2$SO$_4$; filter; collect the filtrate; and concentrate under reduced pressure. Triturate the resulting gum with a minimal volume of diethyl ether and isolate the resulting white solid by filtration to provide the title compound (77 mg, 0.16 mmol, 100%). ESMS (m/z) ($^{35}$Cl/$^{37}$Cl) 474/476 (M+H)$^+$.

EXAMPLE 7

4-Chloro-2-(2-((1S,2S)-2-(1-(p-tolyl)piperidine-4-carboxamido)cyclopentyl)ethyl)benzoic acid

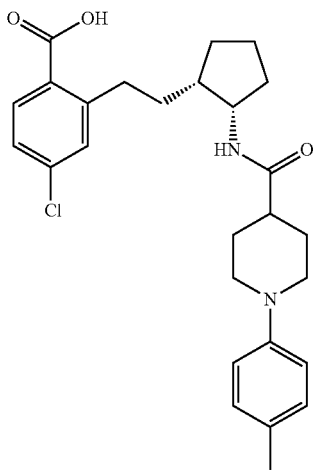 [SMILES: Cc1ccc(N2CCC(C(=O)N[C@H]3CCC[C@H]3CCc3cc(Cl)ccc3C(=O)O)CC2)cc1]

Add 5.0 N aqueous sodium hydroxide (1.0 mL, 5.0 mmol) to a solution of methyl 4-chloro-2-(2-((1S,2S)-2-(1-(p-tolyl)piperidine-4-carboxamido)cyclopentyl)ethyl)benzoate (95 mg, 0.196 mmol) in methanol (2 mL) and tetrahydrofuran (2 mL). Heat the mixture at 70° C. for 4 hours. Add 5 N aqueous HCl (1.0 mL) and remove the volatiles to provide a solid. Triturate the solid with a small amount of methanol and then add water. Collect the beige solid by filtration to provide the title compound (60 mg, 0.13 mmol, 65%). ESMS (m/z) ($^{35}$Cl/$^{37}$Cl) 469/471 (M+H)$^+$.

EXAMPLE 8

4-Chloro-2-(2-((1S,2S)-2-(1-(4-(trifluoromethyl)phenyl)piperidine-4-carboxamido)cyclopenyl)ethyl)benzoic acid

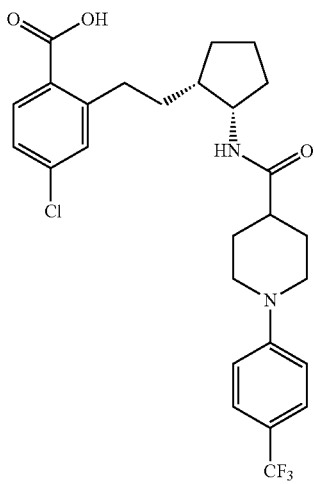 [SMILES: O=C(O)c1ccc(Cl)cc1CC[C@@H]1CCC[C@@H]1NC(=O)C1CCN(c2ccc(C(F)(F)F)cc2)CC1]

Dissolve methyl 4-chloro-2-(2-((1S,2S)-2-(1-(4-(trifluoromethyl)phenyl) piperidine-4-carboxamido)cyclopentyl)ethyl)benzoate (1.4 g, 2.61 mmol) in tetrahydrofuran (26 mL). Add aqueous LiOH (0.5 M, 21 mL). Heat the mixture to 110° C. for 2 hours and then heat at 100° C. for 3.5 hours. Allow the mixture to cool to ambient temperature and stir overnight. Heat the mixture at 100° C. until all the starting material has been consumed (about 5 hours). Cool the reaction to room temperature and evaporate the solvent. Acidify the residue to pH 5 with 5 N aqueous HCl. Collect the resulting white precipitate; wash with water; and dry under vacuum to provide the title compound (1.34 g, 2.56 mmol, 98%). ESMS (m/z) ($^{35}$Cl/$^{37}$Cl) 523/525 (M+H)$^+$.

EXAMPLE 9

4-Chloro-2-(2-((1S,2S)-2-(1-(6-(trifluoromethyl)pyridin-3-yl)piperidine-4-carboxamido)cyclopentyl)ethyl)benzoic acid

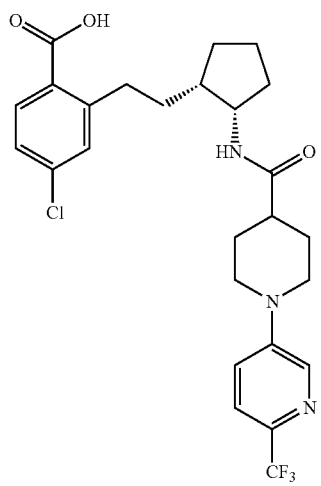 [SMILES: O=C(O)c1ccc(Cl)cc1CC[C@@H]1CCC[C@@H]1NC(=O)C1CCN(c2ccc(C(F)(F)F)nc2)CC1]

Add aqueous NaOH (1.0 M, 0.5 mL) to a solution of methyl 4-chloro-2-(2-((1S,2S)-2-(1-(6-(trifluoromethyl)pyridin-3-yl)piperidine-4-carboxamido)cyclopentyl)ethyl)benzoate (58 mg, 0.11 mmol) in methanol (3.0 mL). Heat the mixture to 50° C. and stir overnight. Add aqueous HCl (5 M, 0.5 mL). Concentrate under reduced pressure. Azeotropically remove water with toluene. Suspend the residue in 20% tetrahydrofuran in EtOAc (10 mL); wash with saturated aqueous NaCl (10 mL); dry over MgSO$_4$; filter; collect the filtrate; and concentrate under reduced pressure to provide the title compound (51 mg, 0.097 mmol, 90%). ESMS (m/z) ($^{35}$Cl/$^{37}$Cl) 524/526 (M+H)$^+$.

EXAMPLE 10

4-Chloro-2-(2-((1S,2S)-2-((S)-3,3-dimethyl-1-(8-methylquinolin-2-yl)piperidine-4-carboxamido)cyclopentyl)ethyl)benzoic acid

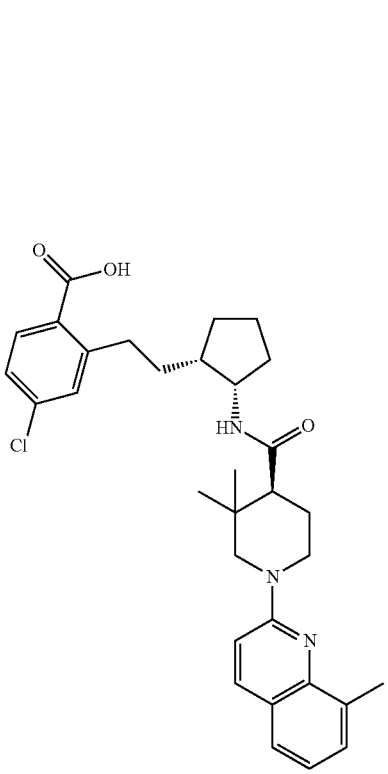 [SMILES: Cc1cccc2ccc(N3CC[C@H](C(=O)N[C@H]4CCC[C@H]4CCc4cc(Cl)ccc4C(=O)O)C(C)(C)C3)nc12]

Dissolve methyl 4-chloro-2-(2-((1S,2S)-2-((S)-3,3-dimethyl-1-(8-methylquinolin-2-yl)piperidine-4-carboxamido)cyclopentyl)ethyl)benzoate (284 mg, 0.505 mmol) in methanol (3 mL) and tetrahydrofuran (3 mL). Add aqueous LiOH (0.5 M, 5 mL). Heat the mixture at 50° C. overnight. Concentrate the solution. Acidify the aqueous mixture to pH 1 using 1 N aqueous HCl. Dilute the mixture with water (20 mL) and stir for 30 minutes. Isolate the slightly yellow precipitate by filtration and dry by pulling air through the filter cake to provide the title compound (174 mg, 0.318 mmol, 63%). ESMS (m/z) ($^{35}$Cl/$^{37}$Cl) 548/550 (M+H)$^+$. $^1$H NMR (400.13 MHz, d-$_6$-DMSO) δ 7.91 (d, J=9.2 Hz, 1H), 7.70-7.68 (m, 2H), 7.47 (d, J=8.0 Hz, 1H), 7.35 (d, J=9.1 1H), 7.23-7.17 (m, 3H), 7.05 (t, J=7.5 Hz, 1H), 4.63-4.60 (m, 1H), 4.23-4.20 (m, 1H), 4.09 (d, J=13.4 Hz, 1H), 3.03-3.00 (m, 2H), 2.83-2.82 (m, 2H), 2.39-2.27 (m, 1H), 1.89-1.87 (m, 11H), 0.96 (s, 3H), 0.91 (s, 3H).

EXAMPLE 11

2-(2-((1S,2S)-2-(1-(4-(Trifluoromethyl)phenyl)piperidine-4-carboxamido)cyclopentyl)ethyl)nicotinic acid

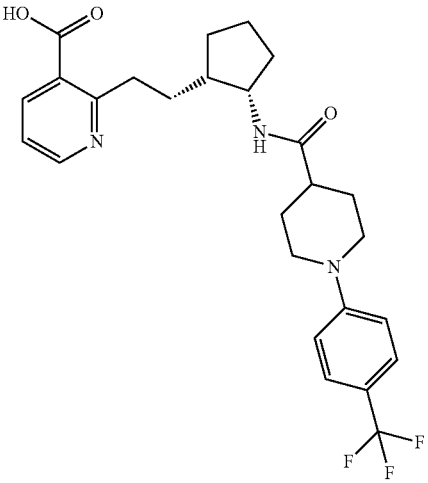

Dissolve ethyl 2-(2-((1S,2S)-2-(1-(4-(trifluoromethyl)phenyl)piperidine-4-carboxamido)cyclopentyl)ethyl)nicotinate (146 mg, 0.282 mmol) in tetrahydrofuran (3 mL) and methanol (1 mL). Add 0.5 M aqueous lithium hydroxide (1.5 mL, 0.75 mmol). Seal the vessel and heat the sealed vessel at 45° C. overnight. Cool the mixture to room temperature and concentrate to remove the volatile organics. Acidify the mixture to pH 3 with 1 N aqueous HCl and collect the resulting white precipitate by filtration. Further acidify the filtrate to pH 1 to obtain a yellow gum. Combine all solutions and isolates and concentrate. Subject the residue by reverse phase column chromatograph, eluting with a gradient of 10% to 55% acetonitrile and water modified with 10 mM (NH$_4$)$_2$CO$_3$ and 5% methanol, to give the title compound as a white solid (50 mg, 0.10 mmol, 36%). ESMS (m/z) 490 (M+H)$^+$.

EXAMPLE 12

4-Methyl-2-(2-((1S,2S)-2-(1-(4-(trifluoromethyl)phenyl)piperidine-4-carboxamido)cyclopentyl)ethyl)benzoic acid

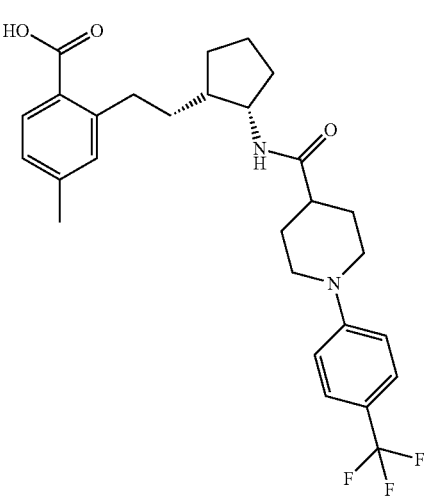

Dissolve ethyl 4-methyl-2-(2-((1S,2S)-2-(1-(4-(trifluoromethyl)phenyl)piperidine-4-carboxamido)cyclopentyl)ethyl)benzoate (369 mg, 0.714 mmol) in tetrahydrofuran (30 mL) and methanol (10 mL) Add aqueous lithium hydroxide (0.5 M, 15 mL). Heat the mixture at 45° C. and stir overnight. After 22 hours, increase the temperature to 70° C. for one hour then store the mixture at 4° C. until heating is resumed. Heat the reaction at 55° C. for 5 hours. Concentrate the mixture, add 5 N HCl to acidify the mixture to pH 1. Stir for 20 minutes. Isolate the white precipitate by filtration. Dry the solid in a 40° C. vacuum chamber to provide the title compound (338 mg, 0.672 mmol, 94%). ESMS (m/z) 503 (M+H)$^+$.

EXAMPLE 13

4-Fluoro-2-(2-((1S,2S)-2-(1-(4-(trifluoromethyl)phenyl)piperidine-4-carboxamido)cyclopentyl)ethyl)benzoic acid

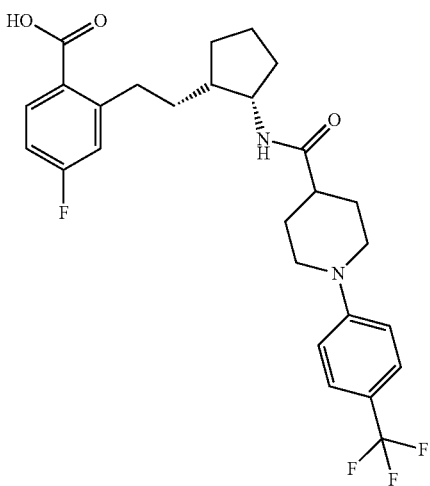

Dissolve methyl 4-fluoro-2-(2-((1S,2S)-2-(1-(4-(trifluoromethyl)phenyl)piperidine-4-carboxamido)cyclopentyl)ethyl)benzoate (127 mg, 0.244 mmol) in tetrahydrofuran (3 mL), methanol (1 mL) and aqueous lithium hydroxide (0.5 M, 1.5 mL). Heat the solution at 45° C. overnight. Partially concentrate the solution to remove organics and bring the aqueous solution to pH 1 with HCl. Isolate the white precipitate by filtration and dry by pulling air through the precipitate to give the title compound (116 mg, 0.229 mmol, 94%). ESMS (m/z) 507 (M+H)$^+$.

EXAMPLE 14

4-Chloro-2-((((1S,2S)-2-(1-(4-(trifluoromethyl)phenyl)piperidine-4-carboxamido)cyclopentyl)methyl)amino)benzoic acid

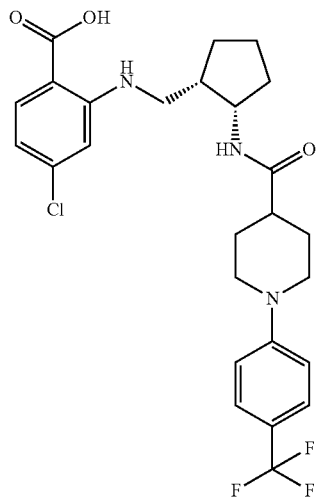 [SMILES: O=C(O)c1ccc(Cl)cc1NC[C@@H]1CCC[C@@H]1NC(=O)C1CCN(c2ccc(C(F)(F)F)cc2)CC1]

Dissolve methyl 4-chloro-2-((((1S,2S)-2-(1-(4-(trifluoromethyl)phenyl) piperidine-4-carboxamido)cyclopentyl)methyl)amino)benzoate (0.25 g, 0.46 mmol) in tetrahydrofuran (10 mL) and methanol (1 mL) Add 5.0 M aqueous sodium hydroxide (0.19 mL, 0.93 mmol). Seal the vessel and heat in a Biotage Initiator™ microwave at 100° C. for 30 minutes. Dilute the mixture with water (50 mL) and add a second lot of 4-chloro-2-((((1S,2S)-2-(1-(4-(trifluoromethyl)phenyl)piperidine-4-carboxamido)cyclopentyl)methyl)amino)benzoic acid (0.29 g, 0.52 mmol) prepared in an analogous manner Add 1.0 N aqueous HCl to the vigorously stirring solution until the pH reaches 7. Isolate the precipitate by filtration to provide the title compound as a white solid (0.50 g, 0.95 mmol, 84% overall yield). ESMS (m/z) ($^{35}$Cl/$^{37}$Cl) 537/539 (M+H)$^+$.

EXAMPLE 15

4-Methyl-2-(((1R,2S)-2-(1-(4-(trifluoromethyl)phenyl)piperidine-4-carboxamido)cyclopentyl)methoxy)benzoic acid

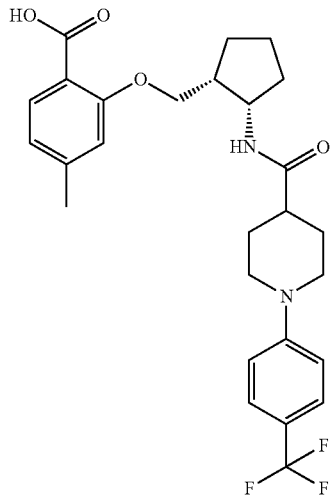

Combine 2-fluoro-4-methylbenzoic acid (50 mg, 0.32 mmol) and N-(((1S,2R)-2-(hydroxymethyl)cyclopentyl)-1-(4-(trifluoromethyl)phenyl)piperidine-4-carboxamide (141 mg, 0.324 mmol), and tetrahydrofuran (3.24 mL). Add sodium hydride (60% in mineral oil, 97 mg, 2.43 mmol) portionwise. Heat the mixture at reflux overnight. Cool the mixture to ambient temperature. Dilute with EtOAc and separate the organic and aqueous phases. Dry the organic phase over $Na_2SO_4$; filter; collect the filtrate; and concentrate under reduced pressure. Subject the residue to a reverse phase flash column chromatography, eluting with 10% to 100% acetonitrile in water. Collect the desired fractions. Remove the solvents and dry the resulting residue under vacuum at 50° C. to provide the title compound as a pale yellow solid (59.4 mg, 0.117 mmol, 36%). ESMS (m/z) 505 $(M+H)^+$.

Prepare the following compounds in Table 5 essentially according to the procedure listed above for Example 15.

TABLE 5

| Ex. No. | Chemical Name | Structure | ESMS (m/z) $(M + 1)^+$ |
|---|---|---|---|
| 16 | 2-(((1R,2S)-2-(1-(4-(Trifluoromethyl)phenyl)piperidine-4-carboxamido)cyclopentyl)methoxy)benzoic acid | 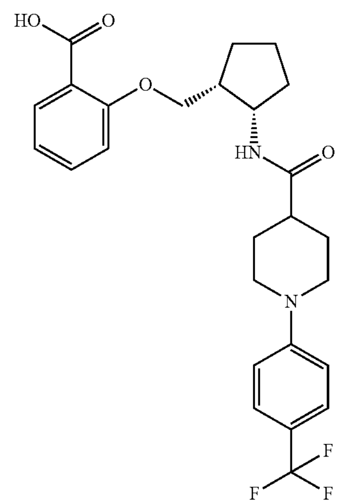 [SMILES: O=C(O)c1ccccc1OC[C@@H]1CCC[C@@H]1NC(=O)C1CCN(c2ccc(C(F)(F)F)cc2)CC1] | 481 |
| 17 | 4-Chloro-2-(((1R, 2S)-2-(1-(4-(trifluoromethyl)phenyl)piperidine-4-carboxamido)cyclopentyl)methoxy)benzoic acid | 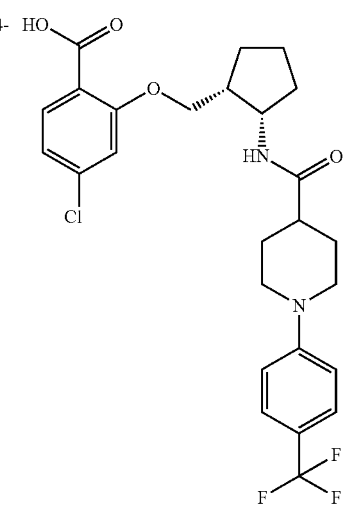 | ($^{35}$Cl/$^{37}$Cl) 525/527 |

EXAMPLE 18

4-Chloro-2-[[(1S,2S)-2-[[1-[3-(trifluoromethyl)phenyl]piperidine-4-carbonyl]amino]cyclohexyl]methylamino]benzoic acid

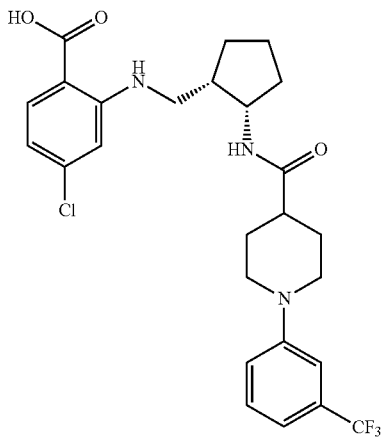 [SMILES: O=C(O)c1ccc(Cl)cc1NC[C@@H]1CCC[C@@H]1NC(=O)C1CCN(c2cccc(C(F)(F)F)c2)CC1]

Dissolve methyl 4-chloro-2-[[(1S,2S)-2-[[1-[3-(trifluoromethyl)phenyl]piperidine-4-carbonyl]amino]cyclohexyl]methylamino]benzoate (0.046 g, 0.083 mmol) in tetrahydrofuran (2 mL), and methanol (1 mL). Add 5 N sodium hydroxide in water (1.00 mL, 5.00 mmol). Stir overnight. Acidify the mixture to pH 7 using a 1 N aqueous hydrogen chloride solution. Concentrate the mixture under reduced pressure to a volume of ~3 mL. Collect the solid by filtration and wash the solid with water. Dry the solid in a vacuum oven at 50° C. overnight to provide the title compound as a white solid (0.032 g, 71%). ESMS (m/z) ($^{35}$Cl/$^{37}$Cl) 538/540 (M+H)$^+$.

EXAMPLE 19

(±)-4-Chloro-2-(2-(trans-2-(1-(4-(trifluoromethyl)phenyl)piperidine-4-carboxamido)cyclopentyl)ethyl)benzoic acid

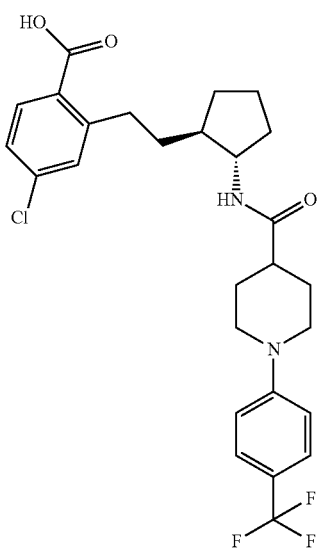 [SMILES: O=C(O)c1ccc(Cl)cc1CC[C@H]1CCC[C@@H]1NC(=O)C1CCN(c2ccc(C(F)(F)F)cc2)CC1]

Dissolve methyl 4-chloro-2-(2-(trans-2-(1-(4-(trifluoromethyl)phenyl)piperidine-4-carboxamido)cyclopentyl)ethyl)benzoate (0.046 g, 0.085 mmol) in tetrahydrofuran (2 mL) and MeOH (0.5 mL). Add aqueous 5M sodium hydroxide (0.034 mL, 0.17 mmol). Stir the mixture at room temperature overnight. Dilute with water (5 mL) and adjust the pH to 4 by dropwise addition of 0.1M aqueous HCl. Extract the aqueous layer with EtOAc (3×10 mL). Combine the organic extracts; wash with brine (25 mL); dry over MgSO$_4$; filter; collect the filtrate; and concentrate under reduced pressure to furnish the title compound as a white solid (0.041 g, 89%). ESMS (m/z) ($^{35}$Cl/$^{37}$Cl) 523/525 (M+H)$^+$.

Biological Assays

Human mPGES-1 Enzyme Inhibition Assay

Human mPGES-1 (Invitrogen™ (Cat#97002RG, clone ID 6374722)) is subcloned into pcDNA3.1 and transiently expressed in HEK-293E cells. Microsomes are prepared from cell pellets based on published methods (Oullet et al., Purification and characterization of recombinant microsomal prostaglandin E synthase-1, Protein Expression and Purification, 26 pp 489-495 (2002); and Thoren et al., Human Microsomal Prostanglandin E Synthase-1, J. Biol Chem. 278(25) pp 22199-22209 (2003)). Briefly, pellets are brought up in homogenization buffer (15 mM Tris-HCl, pH 8.0; 0.25 M sucrose; 0.1 mM ethylenediaminetetraacetic acid (EDTA); 1 mM glutathione) and sonicated 5×30 seconds on ice. Homogenate is centrifuged at 5,000×g for 10 minutes at 4° C. The supernatant fraction is decanted and loaded into Beckman Quick-Seale tubes and centrifuged at 150,000×g for 90 minutes at 4° C. The supernatant fraction is discarded by decantation and the pellets are re-suspended in assay buffer (10 mM sodium phosphate, pH 7.0; 10% glycerol; 2.5 mM glutathione; Complete Protease Inhibitor Cocktail™ (Roche)). Protein concentration is determined using the Pierce Coomassie Plus™ reagent.

For the enzyme assay, the microsomes are diluted into assay buffer and 14 μL/well of the resulting solution is added to the wells of a 384 well assay plate. Compound dilution plates (Nunc Cat#249944) are generated on a Tecan_MC384™, and 4 μL/well are added to the assay plates. Prostaglandin H$_2$ (PGH$_2$) is diluted into assay buffer immediately before use and 14 μL/well is added to the assay plates. Final concentrations are 6.52 μg/mL microsomes and 1.67 μM PGH$_2$. After a 2.5 minute incubation at room temperature, 2.5 μL/well of 1 mg/mL SnCl$_2$ in 0.5 N HCl is added to stop the reaction. Five μL of the stopped reaction are transferred to a 384 well plate containing 45 μL of 0.1% formic acid, and the plates are stored at −80° C. The plates are shipped to Agilent Technologies, formerly Biocius Lifesciences (Wakefield, Mass. 01880) for standard LC/MS analysis for PGE$_2$. The data are used to calculate the IC$_{50}$ (μM). The compounds of the Examples inhibit human mPGES-1 with an IC$_{50}$ μM value of less than 100 nM. This result demonstrates that the compound of Example 1 is a potent inhibitor of the mPGES-1 enzyme in an isolated enzyme preparation.

Cell Based Assay for Measuring Eicosanoid Selectivity

Human epithelial lung carcinoma cell line A549 is obtained from ATCC (CCL-185) and maintained in cell growth medium (Kaighn's F12 cell culture medium+10% fetal bovine serum (FBS)), under standard 5% $CO_2$ humidified atmosphere at 37° C. The cells are passaged at 1:3 twice per week.

For the assays, cells are harvested from flasks by washing once with phosphate buffered saline (PBS), then once with Trypsin-EDTA. After 3-5 minutes at 37° C., the cells are suspended in cell growth medium and centrifuged at 2,000 rpm, 25° C., for 5 minutes. The supernatant is aspirated and the cell pellet is re-suspended in cell growth medium. The cell number is determined by counting an aliquot of cells which has been diluted in PBS and Trypan blue on a hemocytometer. Cells are plated at 40,000/well in 96 well Falcon plates 24 hours prior to treatment. Compounds are diluted in DMSO to 100× of the final concentration in Screen Mates tubes. The medium is removed from the cells and fresh medium (90 μL/well) is added to the cells. The compounds are added at 1 μL/well, n=2, to give seven concentrations each. Cells are pretreated with compounds for 30 minutes at 37° C., 5% $CO_2$. Prostaglandin $E_2$ production is induced by the addition of recombinant human interleukin 1β (rhIL-1β) diluted in cell growth medium to 10× final. A 10 μL/well aliquot is added to give a final rhIL-1β concentration of 0.1 ng/mL. The treatment period is approximately 18 hours. Conditioned medium is removed to v-bottom polypropylene plates. The conditioned medium is assayed for levels of $PGE_2$ and prostaglandin $I_2$ ($PGI_2$) by specific enzyme immune-assay (EIA), according to the manufacturer's protocols (Cayman). Briefly, conditioned medium (1 μL) is added to each well of a 96 well plate coated with a capture antibody and containing EIA buffer (49 μL) supplied by the manufacturer. The tracer is diluted with the EIA buffer (50 μL). The detection antibody is diluted with the EIA buffer (50 μL). The plate is covered with adhesive sealing film and is incubated for 1 hour at room temperature on an orbital shaker at 100 rpm. The wash buffer is diluted into MILLIPORE purified water, and the plate is washed 5×350 μL/well, using a plate washer. The substrate (Ellman's reagent) is diluted with MILLIPORE purified water and then added to the plate at 200 μL/well. After approximately 90-120 minutes at room temperature on an orbital shaker at 100 rpm, the plates are read at A412 on a plate reader. A standard curve of $PGE_2$ is used to calibrate the sample. Example 1 inhibits $PGE_2$ formation in this assay with an $IC_{50}$ of 0.0053 μM.

Human whole Blood Assay

Blood is collected from normal volunteer donors into sodium heparin VACUTAINER tubes. Donors are selected, in part, on their confirmation that they have not taken NSAIDs, aspirin, Celebrex®, or glucocorticoids within two weeks of the donation. All tubes/donor are pooled into 250 mL Corning conical centrifuge tubes and 436.5 μL/well is distributed into deep well polypropylene plates. Compounds are diluted in DMSO to 100× final and 4.5 μL/well in duplicate or triplicate is added to give 7 point curves. The blood is pretreated with compounds at 37° C., 5% $CO_2$, in a humidified atmosphere, covered with a MicroClime Environmental Microplate lid, for 30 minutes after which 9 μL/well of a solution of 5 mg/mL of lipopolysaccharide (LPS, Sigma, serotype 0111:B4) in 1 mg/mL BSA/PBS is added to give a final LPS concentration of 100 μg/mL. The plates are incubated for 20-24 hours, at 37° C., 5% $CO_2$, in a humidified atmosphere. The plates are tightly sealed with the aluminum foil lids and are chilled on ice for approximately 1 hour. Then the plates are centrifuged at 1,800×g, 10 minutes, 4° C., in an Eppendorf 5810R centrifuge. Plasma is removed from the cell layer using the Rainin L200 with sterile filtered tips and transferred to v-bottom polypropylene plates. One hundred microliters is quantitatively transferred to Costar cluster tubes blocks and 400 μL/well of the methanol stop reagent and internal standards, $d_4$-$PGE_2$, $d_4$-$PGF_{2\alpha}$, and $d_4$-$TXA_{2\beta}$ are added. Samples are vortexed for 5 minutes and are placed at −20° C. for at least one hour. Samples are centrifuged for 10 minutes at 4000 rpm in an Eppendorf 5810R.

Solid phase extraction is performed using Waters HLB 30 mg/bed 96 well plates on a vacuum manifold: Step 1, the matrix is washed with methanol (1 mL), followed by 0.1% formic acid in water (1 mL); Step 2, 400 μL sample is applied along with 0.1% formic acid in water (900 μL) and allowed to bind for 5 minutes; Step 3, the matrix is washed with 0.1% formic acid in water (600 μL), followed by 80/20 water/methanol (600 μL); Step 4, the products are eluted with 2-500 μL volumes of EtOAc; Step 5 the samples are dried under nitrogen and reconstituted in 75/25 water/acetonitrile with 0.1% formic acid (50 μL). The products are analyzed by LC/MS/MS. Example 1 inhibits $PGE_2$ formation in this assay with an $IC_{50}$ of 0.0059±0.0034, n=6, >95% confidence. This result supports that Example 1 inhibits $PGE_2$ synthesis in human whole blood.

What is claimed is:
1. A compound of Formula 1:

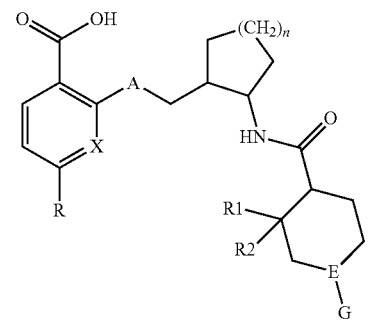

wherein:
n is 1 or 2;
A is selected from: —$CH_2$—, —NH—, and —O—;
E is CH or N ;
X is N or CH;
R is selected from: H, —$CH_3$, F, and Cl;
R1 and R2 are each independently H or $CH_3$; and
G is selected from:

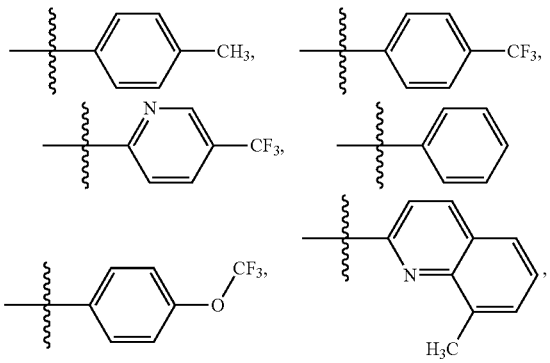

-continued

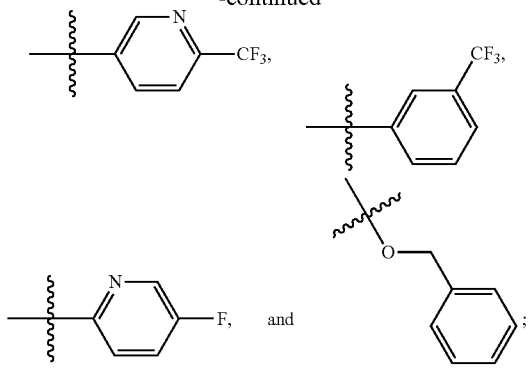

provided that when G is

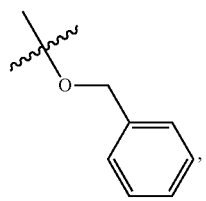 [SMILES: *OCc1ccccc1]

E is CH; and provided that when A is —NH— or —O—, X is CH;
or a pharmaceutically acceptable salt thereof.

2. A compound according of Formula 2:

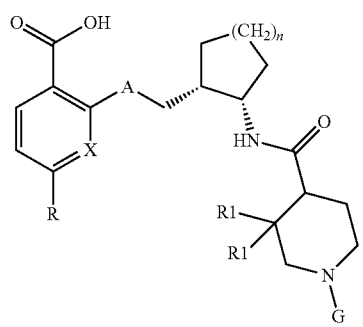

wherein:
n is 1 or 2;
A is selected from: —CH₂—, —NH—, and —O—;
X is N or CH;
A is selected from: —CH₂—, —NH—, and —O—;
R is selected from: H, —CH₃, F, and Cl;
Each R1 is independently H or CH₃; and
G is selected from:

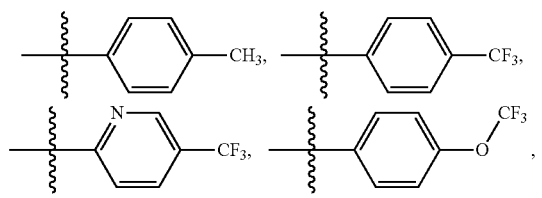

-continued

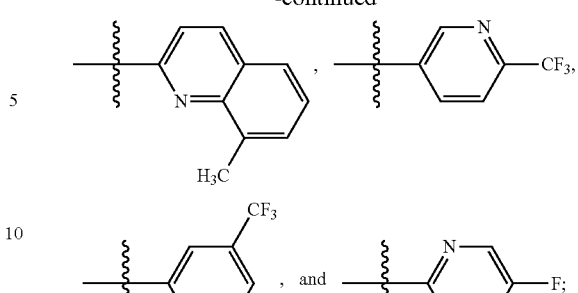

provided that when A is —NH— or —O—, X is CH;
or a pharmaceutically acceptable salt thereof.

3. A compound according to claim 1 wherein n is 1.

4. A compound according to claim 1 wherein E is N.

5. A compound according to claim 1 wherein R is selected from: H, —CH₃, and F.

6. A compound according to claim 5 wherein R is H.

7. A compound according to claim 1 wherein A is —O— or —CH₂—.

8. A compound according to claim 7 wherein A is —CH₂—.

9. A compound according to claim 1 wherein G is selected from:

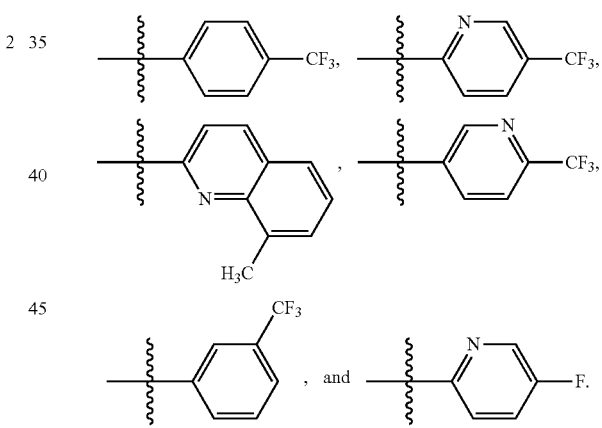

10. A compound according to claim 9 wherein G is selected from:

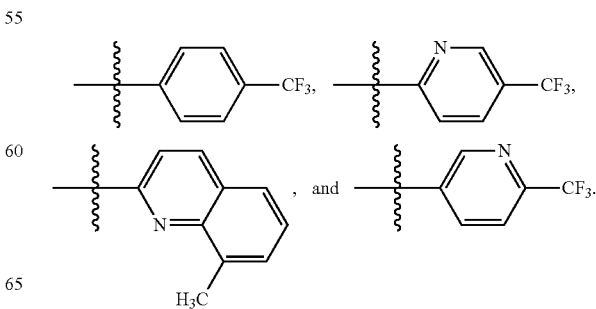

11. A compound according to claim 10 wherein G is

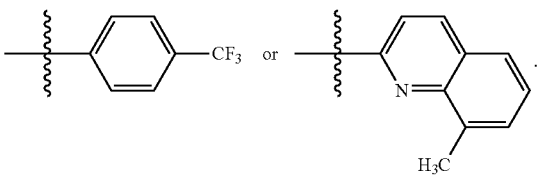

12. A compound according to claim 1 wherein X is —CH—.

13. A compound according to claim 1 wherein R1 and R2 are H.

14. A compound which is:

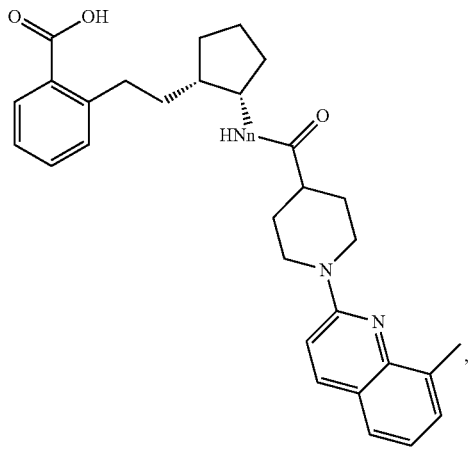

or a pharmaceutically acceptable salt thereof.

15. A compound according to claim 14 wherein the pharmaceutically acceptable salt is a sodium salt.

16. A pharmaceutically acceptable composition comprising a compound according to claim 1, or a pharmaceutically acceptable salt thereof, and at least one of a pharmaceutically acceptable carrier, diluent or excipient.

17. A method of treating a patient in need of treatment for pain associated with arthritis, said method comprising administering to the patient an effective amount of a compound, or a pharmaceutically acceptable salt thereof, according to claim 1.

18. A method of treating a patient in need of treatment for pain associated with osteoarthritis, said method comprising administering to the patient an effective amount of a compound, or a pharmaceutically acceptable salt thereof, according to claim 1.

19. A method of treating a patient in need of treatment for inflammation associated with arthritis, said method comprising administering to the patient an effective amount of a compound, or a pharmaceutically acceptable salt thereof, according to claim 1.

20. A method of treating a patient in need of treatment for inflammation associated with osteoarthritis, said method comprising administering to the patient an effective amount of a compound, or a pharmaceutically acceptable salt thereof, according to claim 1.

21. A method of treating a patient in need of treatment for pain or inflammation associated with arthritis, said method comprising administering to the patient an effective amount of a pharmaceutically acceptable composition according to claim 16.

22. A method of treating a patient in need of treatment for pain or inflammation associated with osteoarthritis, said method comprising administering to the patient an effective amount of a pharmaceutically acceptable composition according to claim 16.

23. A pharmaceutically acceptable composition comprising a compound according to claim 14, or a pharmaceutically acceptable salt thereof, and at least one of a pharmaceutically acceptable carrier, diluent or excipient.

24. A method of treating a patient in need of treatment for pain or inflammation associated with arthritis or osteoarthritis, said method comprising administering to the patient an effective amount of a compound, or a pharmaceutically acceptable salt thereof, according to claim 14.

* * * * *

UNITED STATES PATENT AND TRADEMARK OFFICE
CERTIFICATE OF CORRECTION

PATENT NO. : 9,969,714 B2
APPLICATION NO. : 15/520078
DATED : May 15, 2018
INVENTOR(S) : Matthew Joseph Fisher et al.

Page 1 of 1

It is certified that error appears in the above-identified patent and that said Letters Patent is hereby corrected as shown below:

On the Title Page

Column 1 (*) (Notice) Line 3:
Please delete the repeated word "days." at the end of the sentence.

Signed and Sealed this
Fourteenth Day of August, 2018

Andrei Iancu
*Director of the United States Patent and Trademark Office*